(12) United States Patent
Mechali et al.

(10) Patent No.: US 9,856,457 B2
(45) Date of Patent: Jan. 2, 2018

(54) USE OF CELLULAR EXTRACTS FOR OBTAINING PLURIPOTENT STEM CELLS

(75) Inventors: Marcel Mechali, Montferrier sur Lez (FR); Olivier Ganier, Montpellier (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 271 days.

(21) Appl. No.: 14/234,192

(22) PCT Filed: Jul. 19, 2012

(86) PCT No.: PCT/EP2012/064164
§ 371 (c)(1),
(2), (4) Date: Mar. 11, 2014

(87) PCT Pub. No.: WO2013/014057
PCT Pub. Date: Jan. 31, 2013

(65) Prior Publication Data
US 2014/0186944 A1   Jul. 3, 2014

(30) Foreign Application Priority Data
Jul. 22, 2011   (EP) ..................................... 11305960

(51) Int. Cl.
*C12N 5/074*   (2010.01)
*C12N 5/16*   (2006.01)

(52) U.S. Cl.
CPC ............. *C12N 5/0696* (2013.01); *C12N 5/16* (2013.01); *C12N 2502/04* (2013.01)

(58) Field of Classification Search
CPC .... C12N 5/0696; C12N 5/16; C12N 2502/04; C12N 2506/1307; C12N 2500/80; C12N 2500/82; C12N 2500/84; C12N 5/0697; C12N 2502/45; C12N 2501/60; C12N 2501/602; C12N 2501/603; C12N 2501/604; C12N 2501/606; C12N 2501/608; C12N 15/873; C12N 15/877; C12N 15/8771; C12N 15/8772; C12N 15/8773; C12N 15/8774; C12N 15/8775; C12N 15/8776; C12N 15/8777; C12N 15/8778
See application file for complete search history.

(56) References Cited

U.S. PATENT DOCUMENTS 4,477,245 A   10/1984   Giachino et al.

FOREIGN PATENT DOCUMENTS

| EP | 1970446 A1 | 9/2008 |
| JP | 4019447 B2 | 10/2007 |
| WO | 2007039258 A1 | 4/2007 |
| WO | 2007047766 A2 | 4/2007 |

OTHER PUBLICATIONS

Miyamoto et al. Cell-Free Extracts from Mammalian Oocytes Partially Induce Nuclear Reprogramming in Somatic Cells. Biology of Reproduction, 2009, vol. 80, pp. 935-943.*
Mikkelson et al. DNA demethylation is necessary for the epigenetic reprogramming of somatic cell nuclei. Nature, 2008, vol. 454, pp. 49-58.*
Simonsson et al. DNA demethylation is necessary for the epigenetic reprogramming of somatic cell nuclei. Nature Cell Biology, 2004, vol. 6, pp. 984-990.*
Koziol et al. Tpt1 Activates Transcription of oct4 and nanog in Transplanted Somatic Nuclei. Current Biology, 2007, vol. 17, pp. 801-807.*
Takahashi et al., Cell, 126: 663-676, 2006.*
Nakagawa et al., Nature Biotechnology, 26(1): 101-106, 2008.*
Okita, Science, 322: 949-953, 2008.*
Gonzalez. PNAS, 106(22): 8918-8922, 2009.*
Kim et al., Cell Stem Cell, 4: 472-476, 2009.*
Alberio et al., "Differential nuclear remodeling of mammalian somatic cells by Xenopus laevis oocyte and egg cytoplasm", Experimental Cell Research, 2005, vol. 307, pp. 131-141.
Arnaud et al., "Stochastic imprinting in the progeny of Dnmt3L -/- females", Human Molecular Genetics, 2006, vol. 15, No. 4, pp. 589-598.
Bernstein et al., "A Bivalent Chromatin Structure Marks Key Developmental Genes in Embryonic Stem Cells", Cell, 2006, vol. 125, pp. 315-326.
Bru et al., "Rapid induction of pluripotency genes after exposure of human somatic cells to mouse ES cell extracts", Experimental Cell Research, 2008, vol. 314, pp. 2634-2642.
Byrne et al., "Nuclei of Adult Mammalian Somatic Cells Are Directly Reprogrammed to oct-4 Stem Cell Gene Expression by Amphibian Oocytes", Current Biology, 2003, vol. 13, pp. 1206-1213.
Diberardino et al., "Gene Reactivation in Erythrocytes: Nuclear Transplantation in Oocytes and Eggs of Rana", Science, 1983, vol. 219, pp. 862-864.

(Continued)

*Primary Examiner* — Thaian N Ton
(74) *Attorney, Agent, or Firm* — Young & Thompson

(57) ABSTRACT

The use of a composition including at least one permeabilized nucleus of a first cell, or at least one permeabilized first cell including the nucleus and an extract of female germinal cells, or eggs, of a multicellular organism, the eggs being blocked in the metaphase II of meiosis, the extract including EGTA, for carrying out a method for obtaining pluripotent stem cells, or tissues derived from the pluripotent stem cells, or of cloning, provided that the process is not for cloning human beings.

2 Claims, 20 Drawing Sheets

(56) References Cited

OTHER PUBLICATIONS

Egli et al., "Developmental reprogramming after chromosome transfer into mitotic mouse zygotes", Nature, 2007, vol. 447, pp. 679-685.
Egli et al., "Mediators of reprogramming: transcription factors and transitions through mitosis", Molecular Cell Biology, Nature Reviews, 2008, vol. 9, pp. 505-516.
Feng et al., "Molecules that Promote or Enhance Reprogramming of Somatic Cells to Induced Pluripotent Stem Cells", Cell Stem Cell, vol. 4, 2009, pp. 301-312.
Ganier et al., "Synergic reprogramming of mammalian cells by combined exposure to mitotic Xenopus egg extracts and transcription factors", PNAS, 2011, vol. 108, No. 42, pp. 17331-17336.
Gurdon et al., "Nuclear Reprogramming in Cells", Science, vol. 322, 2008, pp. 1811-1815.
Gurdon et al., "Nuclear reprogramming and stem cell creation", PNAS, 2003, vol. 100, Suppl. 1, pp. 11819-11822.
Gurdon et al., "Nuclear Transfer and iPS May Work Best Together", Cell Stem Cell, vol. 2, 2008, pp. 135-138.
Hanna et al., "Direct cell reprogramming is a stochastic process amenable to acceleration", Nature, 2009, vol. 462, pp. 595-601.
Hanna et al., "Pluripotency and Cellular Reprogramming: Facts, Hypotheses, Unresolved Issued", Cell, vol. 143, 2010, pp. 508-525.
Hansis et al., "Nuclear Reprogramming of Human Somatic Cells by Xenopus Egg Extract Requires BRG1", Current Biology, vol. 14, 2004, pp. 1476-1480.
Hochedlinger et al., "Nuclear reprogramming and pluripotency", Nature, 2006, vol. 441, pp. 1061-1067.
Hochedlinger et al., "Epigenetic reprogramming and induced pluripotency", Development, 2009, vol. 136, pp. 509-523.
Huangfu et al., "Induction of pluripotent stem cells by defined factors is greatly improved by small-molecule compounds", Nature Biotechnology, vol. 26, No. 7, 2008, pp. 795-797.
Irizarry et al., "Exploration, normalization, and summaries of high density oligonucleotide array probe level data", Biostatistics, 2003, vol. 4, No. 2, pp. 249-264.
Jaenisch et al., "Stem Cells, the Molecular Circuitry of Pluripotency and Nuclear Reprogramming", Cell, vol. 132, 2008, pp. 567-582.
Kanai-Azuma et al., "Depletion of definitive gut endoderm in Sox17-null mutant mice", Development, 2002, vol. 129, pp. 2367-2379.
Kikyo et al., "Active Remodeling of Somatic Nuclei in Egg Cytoplasm by the Nucleosomal ATPase ISWI", Science, 2000, vol. 289, pp. 2360-2362.
Lai et al., "Advancements in reprogramming strategies for the generation of induced pluripotent stem cells", J. Assist Reprod. Genet., 2011, vol. 28, pp. 291-301.
Lemaitre et al., "Mitotic Remodeling of the Replicon and Chromosome Structure", Cell, 2005, vol. 123, pp. 787-801.
Leonard et al., "Induction of DNA Synthesis in Amphibian Erythroid Nuclei in Rana Eggs following Conditioning in Meiotic Oocytes", Developmental Biology, 1982, vol. 92, pp. 343-355.

Li et al., "Nuclear transfer: Progress and quandaries", Reproductive Biology and Endocrinology, 2003, vol. 1, pp. 2-6.
Maherali et al., "Directly Reprogrammed Fibroblasts Show Global Epigenetic Remodeling and Widespread Tissue Contribution", Cell Stem Cell, 2007, vol. 1, pp. 55-70.
McKay, Ron, "Studies of stem cells will help in understanding the development and function of organs in mammals. They may also offer a way of treating diseases ranging from liver failure to Parkinson's disease", Nature, 2000, vol. 406, pp. 361-364.
Menut et al., "DNA Replication and Chromatin Assembly Using Xenopus Eggs or Embryos", Advances in Molecular Biology: A comparative Methods Approach to the Study of Oocytes and Embryos, 1999, pp. 196-226.
Miyamoto et al., "Reprogramming Events of Mammalian Somatic Cells Induced by Xenopus laevis Egg Extracts", Molecular Reproduction and Development, 2007, vol. 74, pp. 1268-1277.
Ng et al., "Epigenetic memory of an active gene state depends on histone H3.3 incorporation into chromatin in the absence of transcription", Nature Cell Biology, 2008, vol. 10, No. 1, pp. 102-109.
Park et al., "Reprogramming of human somatic cells to pluripotency with defined factors", Nature, 2008, vol. 451, pp. 141-146.
Pevny et al., "A role for SOX1 in neural determination", Development, 1998, vol. 125, pp. 1967-1978.
Santos et al., "Epigenetic Marking Correlates with Developmental Potential in Cloned Bovine Preimplantation Embryos", Current Biology, 2003, vol. 13, pp. 1116-1121.
Sylvestre et al., "Investigating the Potential of Genes Preferentially Expressed in Oocyte to Induce Chromatin Remodeling in Somatic Cells", Cellular Reprogramming, 2010, vol. 12, No. 5, pp. 519-528.
Takahashi et al., "Induction of Pluripotent Stem Cells from Mouse Embryonic and Adult Fibroblast Cultures by Defined Factors", Cell, 2006, vol. 126, pp. 663-676.
Taranger et al., "Induction of Dedifferentiation, Genomewide Transcriptional Programming, and Epigenetic Reprogramming by Extracts of Carcinoma and Embryonic Stem Cells", Molecular Biology of the Cell, 2005, vol. 16, pp. 5719-5735.
Todaro et al., "Quantitative Studies of the Growth of Mouse Embryo Cells in Culture and Their Development into Established Lines", The Journal of Cell Biology, 1963, vol. 17, pp. 299-313.
Wakayama et al., "Nuclear transfer into mouse zygotes", Nature Genetics, 2000, vol. 24, pp. 108-109.
Wernig et al., "In vitro reprogramming of fibroblasts into a pluripotent ES-cell-like state", Nature, 2007, vol. 448, pp. 318-324.
Yamanaka et al., "Nuclear reprogramming to a pluripotent state by three approaches", Nature, 2010, vol. 465, pp. 704-712.
Yang et al., "Nuclear reprogramming of cloned embryos and its implications for therapeutic cloning", Nature Genetics, 2007, vol. 39, No. 3, pp. 295-302.
Yu et al., "Induced Pluripotent Stem Cell Lines Derived from Human Somatic Cells", Science, 2007, vol. 318, pp. 1917-1920.
Chiang et al., Abstract of "273 Selection of Pluripotent Stem Cells Induced by Xenopus Egg Extracts," Reproduction, Fertility and Development, 2008, vol. 21, No. 1, pp. 234.
Stadtfeld, et al., "Induced Pluripotency: history, mechanisms, and applications," Genes & Development, 2010, vol. 24, pp. 2239-2263.
Japanese Office Action of corresponding Japanese Application No. 2014-520663, dated May 17, 2016.

* cited by examiner

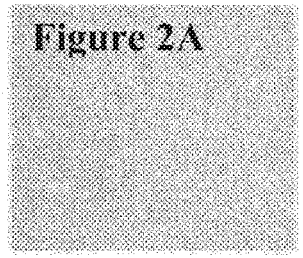
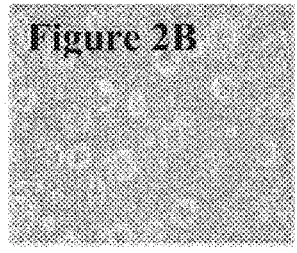
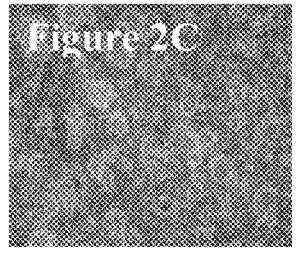
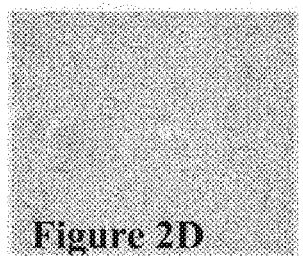
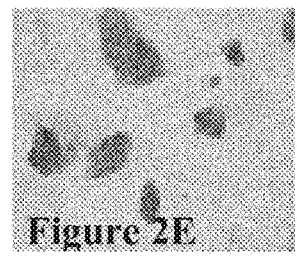
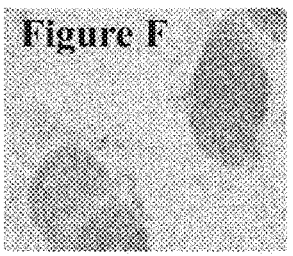
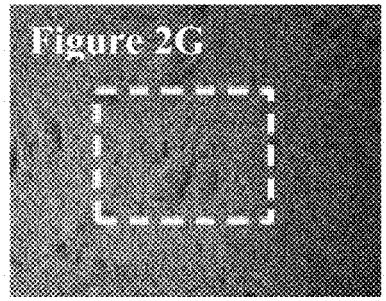
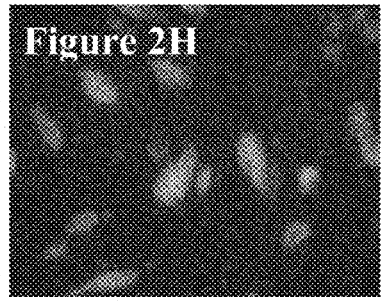
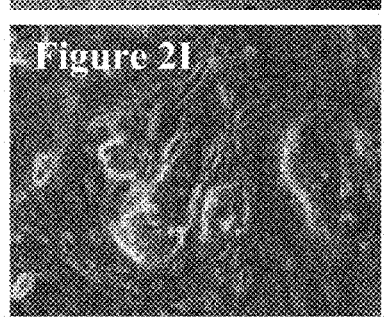

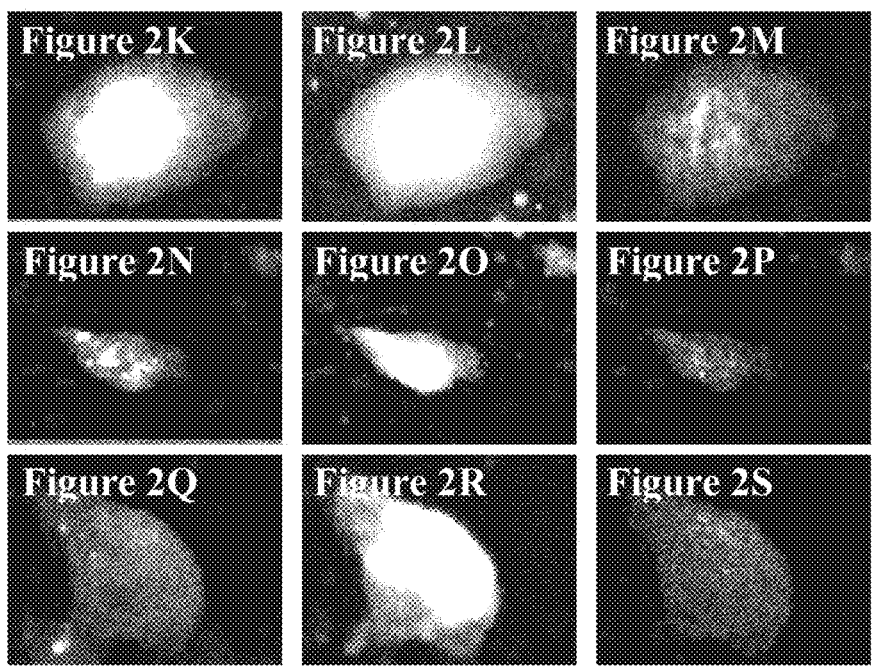
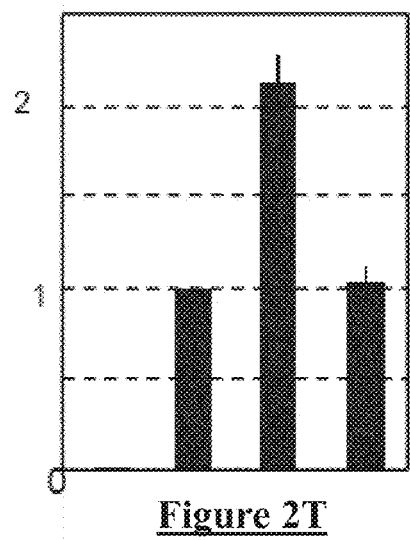
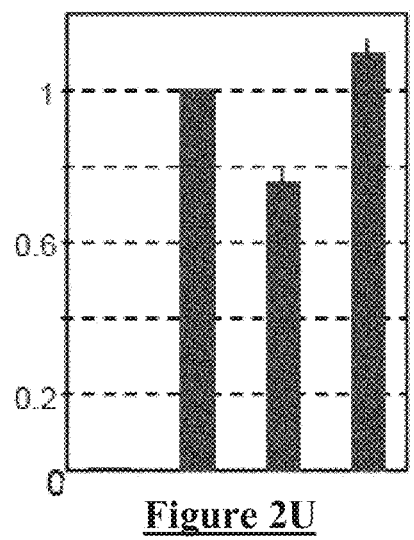
Figure 2T
Figure 2U

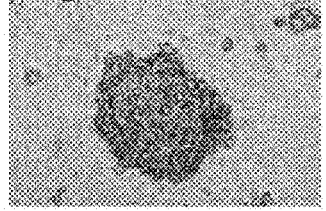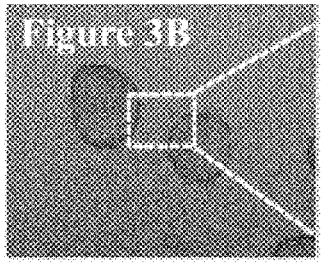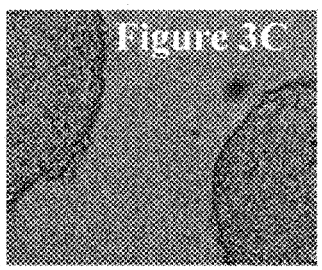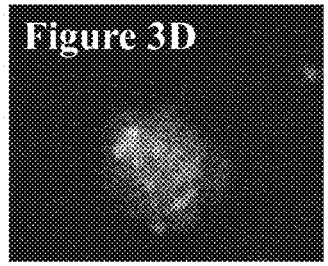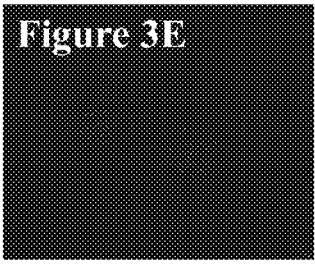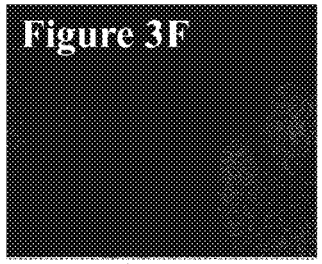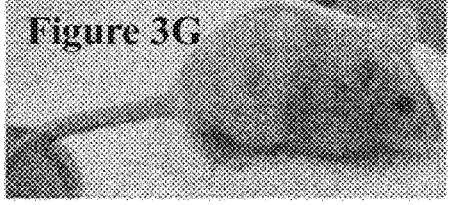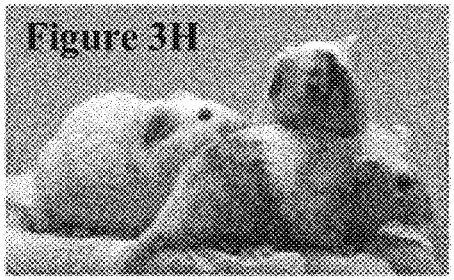

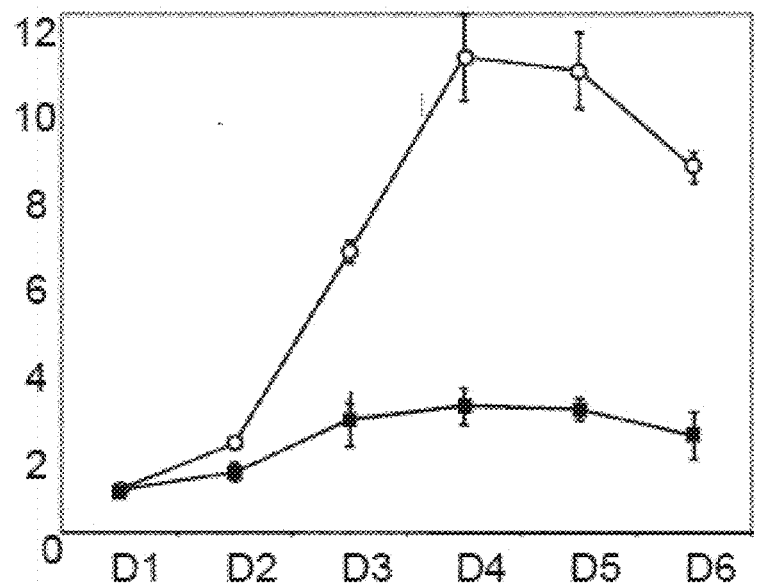
Figure 4A
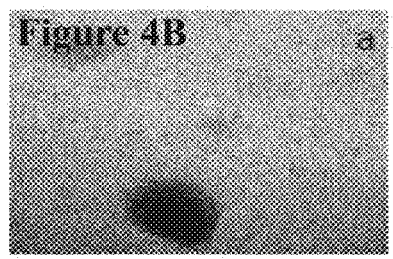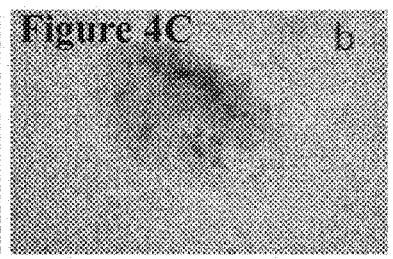
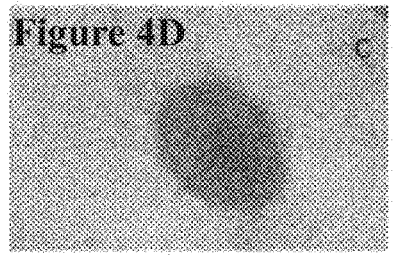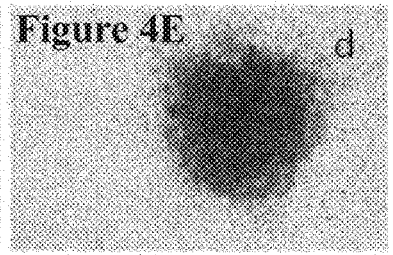
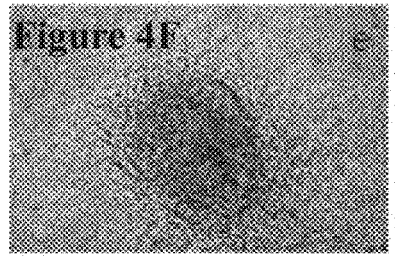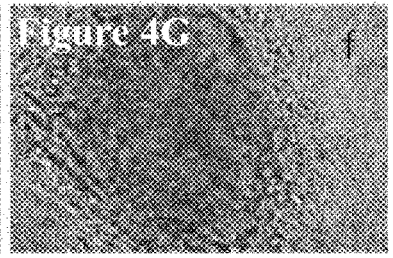

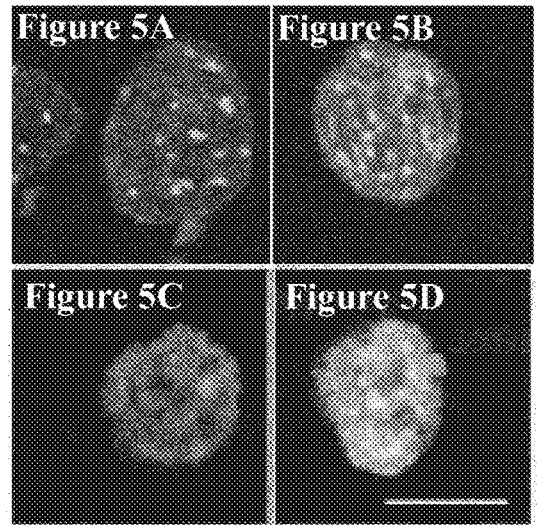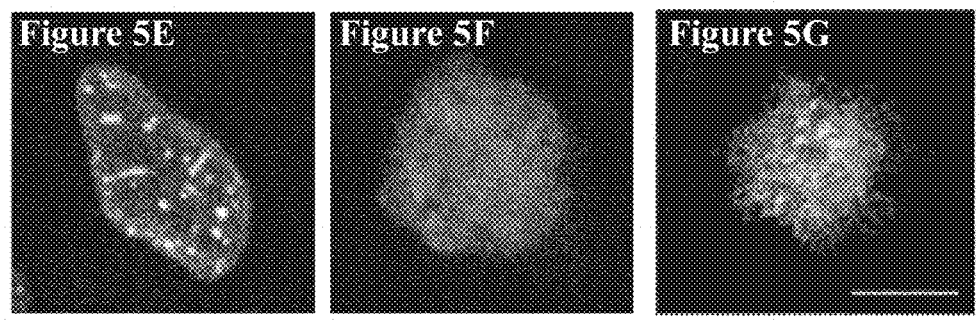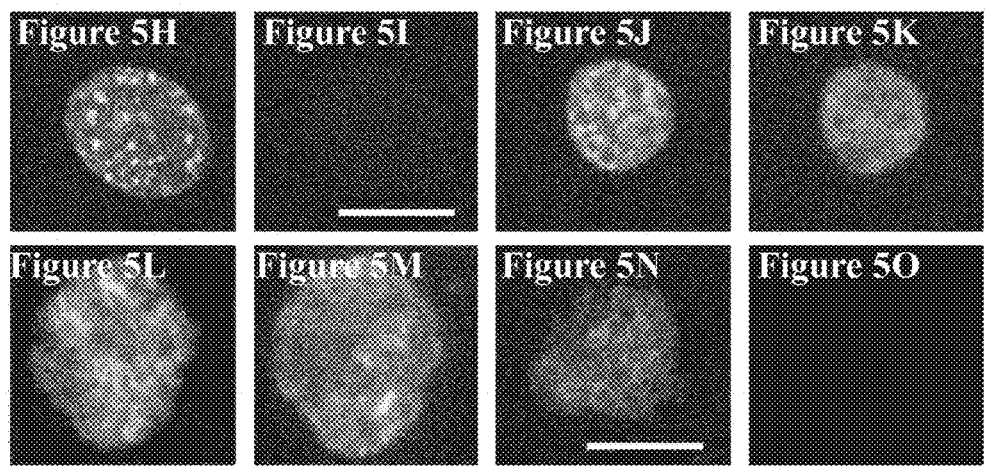

USE OF CELLULAR EXTRACTS FOR OBTAINING PLURIPOTENT STEM CELLS

The present invention relates to the use of cellular extracts for obtaining pluripotent stem cells, in particular for reprogramming differentiated cells.

Nuclear transfer is a powerful method that can be used to obtain new sources of multipotential cells from differentiated tissues and to produce cloned animals. By transplanting nuclei from differentiated amphibian or mammalian cells into enucleated eggs, blastula or blastocyst embryos can be obtained which can develop into entire animals or used to form a wide range of tissues and cell types [Gurdon, et al. (2003). *Proc Natl Acad Sci USA* 100 *Suppl* 1, 11819-11822]. The potential ability to deliver supplies of multipotential cells, which hold great promise for cell-based therapies for numerous disorders, makes nuclear transfer an appealing alternative to the difficult practice of directly isolating natural stem cells from normal adult tissues [McKay, R. (2000). *Stem cells—hype and hope. Nature* 406, 361-364].

It has been recently suggested that different reprogramming strategies could be associated together to synergize their efficiencies [Gurdon J & Murdoch A (2008) *Cell Stem Cell* 2:135-138]. Several attempts have been made by using cellular extracts to reprogram somatic cells, but they failed to reproduce the range of effects obtained by NT.

In NT experiments, it is the exposure of transplanted nuclei to the cytoplasm of the receiving oocyte that induces the reprogramming. Since eggs naturally contain all the genetic and epigenetic factors essential for totipotency, embryonic stem cells obtained by nuclear transfer are closer to natural embryonic stem cells. However, this is hard to mimic in vitro due to the difficulty to obtain large quantities of mammalian oocytes.

Despite its many advantages, however, nuclear transplantation is often inefficient due to the difficulty involved in completely reprogramming differentiated adult nuclei for the events of early development. Indeed, it is known that the ability of the egg to reset the epigenetic marks of adult donor cells is determinant for the efficiency of nuclear cloning. Identifying the specific epigenetic properties of differentiated cell nuclei that must be reset before development can begin anew, and how such resetting can be efficiently achieved, thus represents a challenge of major biological and medical significance.

First Generation

Various methods have been identified that can enhance the efficiency of nuclear transplantation.

In amphibians, for instance, cloning efficiency is substantially improved by serial nuclear transfers. This consists of transferring a nucleus from a differentiated donor cell to an enucleated egg, allowing the cell to undergo several divisions, and then using the daughter nuclei as donors for a second nuclear transfer experiment [Gurdon, J. B. (1962). *J Embryol Exp Morphol* 10, 622-640]. Injections of nuclei into maturing oocytes instead of eggs [DiBerardino, M. A., and Hoffner, N. J. (1983) *Science* 219, 862-864] led to the hypothesis that components of maturing oocytes may enable the injected nucleus to respond to DNA synthesis-inducing factors in activated eggs [Leonard, et al. (1982) *Dev Biol* 92, 343-355]. One possible factor contributing to the low efficiency of cloning experiments is that the chromosome organization of differentiated adult nuclei may not be well adapted for DNA replication.

Animal cloning represents a major challenge in various fields, from the conservation of animal species, the production of proteins, such as therapeutic proteins, by cloned animals, to the therapeutic cloning, particularly for obtaining stems cells useful for autologous transplants.

However, the efficiency of the current cloning techniques needs to be improved to in order to contemplate large scale applications.

The deficiency of the prior art have been partially solved.

The international application WO 2007/039258 discloses the use of a cellular extract for remodeling chromosomes, in order to carry out a process for reprogramming, or cloning cells. The aim of this application is essentially to reprogram chromosomes. Thus, this document only partially solves the problem regarding the complete dedifferentiation of differentiated cells.

So the techniques of NT needed to be improved.

Second Generation

More recently, other approaches have been made in order to enhance the efficiency of cloning and the efficiency of the method of reprogramming differentiated cells.

For instance, the European patent application EP 1 970 446 discloses the induction of pluripotency, in somatic cells, by the ectopic expression of the four transcription factors: Oct4, Klf4, Sox2 and c-Myc (OKSM). This document demonstrate that the above four factors allow to obtain induced pluripotent stem (iPS) cells, which are highly similar to embryonic stem (ES) cells.

Notably, murine iPS cells have a complete developmental potential as demonstrated by their capacity to form teratomas, generate chimeras and contribute to the germline. However, the efficiencies of both iPS cell production and nuclear transfer (NT) remain low and most of the obtained reprogrammed cells appear to be only partially reprogrammed.

Thus, additional factors may be needed to improve them [Feng B, et al. (2009) *Cell Stem Cell* 4:301-312; Huangfu D, et al. (2008) *Nat Biotechnol* 26:795-797] and many efforts have been done over the last years to optimize these procedures.

A recent review [Lai et al. (2011) *J. Assist Reprod Genet*, Mar. 9, 2011] summarizes the improvements of the iPS technologies since its first disclosure (see EP1970446), and conclude that up to date, many challenges need to be overcome, in particular regarding the efficiency.

Therefore, there is a need to provide improvement of the iPS technologies to avoid the deficiencies of the methods disclosed in the art.

The aim of the invention is to overcome such deficiencies.

One particular aim of the invention is to provide a new method that increases the efficiency of dedifferentiation of differentiated cells.

Another aim of the present invention is to provide a composition carrying out said method. Another aim of the invention is also to provide a process for obtaining multipotent or totipotent stem cells of pluricellular organisms.

The invention relates to the use of a composition comprising:
at least one permeabilized nucleus of a first cell, or at least one permeabilized first cell comprising said nucleus
said first cell being an induced pluripotent stem cell, i.e. iPS cell, originating from a multicellular organism,
and
an isolated extract of female germinal cells, or of eggs, of a multicellular organism, said eggs being blocked in the metaphase II of meiosis, said extract comprising EGTA,
for carrying out a method
for obtaining pluripotent stem cells, or tissues derived from said pluripotent stem cells, or of cloning, in particular, of cloning provided that said process is not for cloning human beings.

The invention is based on the unexpected observation made by the Inventors that the combination of cellular extracts of eggs of pluricellular cells and genes allowing the dedifferentiation of differentiated cells act synergistically to significantly enhance the cell reprogramming, i.e. cellular dedifferentiation of differentiated cells, and thus enhance nuclear transfer and cloning obtained by the techniques of the prior art: iPS and nuclear extract.

The expression "germinal cell" refers to a cell susceptible to form the gametes.

The expression "female germinal cell", also called "egg" relates a cell at any stage of the oogenesis, particularly primordial germ cells, oogonia and oocytes.

The germinal cell extract is made from eggs which are arrested at the metaphase stage of the second meiotic division.

The "extract of female germinal cells, or eggs" is a cell extract obtained by the implementation of the process as described in Menut et al. [Menut et at (1999) *Advances in Molecular Biology: A comparative Methods Approach to the Study of Oocytes and Embryos*, ed Richter J D (OxfordUniversity Press), pp 196-226, 2001] (referred as CSF extract).

The above extract is "isolated", which means that said extract is obtained in vitro. This extract is thus completely different from a cell or a part of cell, such as spheroplast or liposomes, which are known in the art.

Extracts are prepared as disclosed in Example 1.

One of the absolute requisite in the extract is the presence of EGTA, a calcium chelating agent which allows the maintaining of the Extract in the metaphase II of the meiosis. Indeed, it is well known in the art that eggs are activated, and exits from metaphase II when calcium enters in cell, following the contact with spermatozoid.

By extension, it is also known that electric chock, needle contact, or any action modifying the plasma membrane of the egg will induce calcium flux in egg, and thus will "unlock" the egg which became activated metaphase II arrested egg: i.e. an interphase egg.

In the invention, it is fundamental that the isolated extract of female germinal cells, or the isolated extract of eggs, is kept in a metaphasic state during its preparation and its use.

It is necessary to control the fragile state induced by EGTA, in which the isolated extract of female germinal cells, or the isolated extract of eggs, is blocked in metaphase. In the invention, the blockage of the isolated extract in metaphase is maintained stable, i.e. the eggs used to obtain the extract of female germinal cells, or of eggs, of a multicellular organism are blocked, in a stable way, in the metaphase II of meiosis.

The stability of the blockage of the isolated extract in metaphase is determined by different ways. Metaphase stage of the extracts can be checked by the structure of the chromatin, the phosphorylation of histone H3 on serine 10. Moreover, the metaphasic stability of the extracts can be followed up of DNA synthesis since extracts blocked in metaphase can replicate efficiently sperm chromatin only if they are previously activated by calcium addition. Tests of the follow up DNA synthesis are achieved by techniques well known in the art, such as measuring [$^{32}$P]αdCTP incorporation (FIG. 12).

In what precedes and what follows, the female germinal cell extract can be replaced by a mitotic non-human early embryo of vertebrates. Said mitotic non-human early embryo of vertebrates may be obtained by the process described in Lemaitre et al. [Lemaitre et at (2005) *Cell* 123:1-15].

The expression "pluricellular organism" (or "multicellular organism") refers to living organisms that are composed of several cells. In said multicellular or pluricellular organisms, the similar cells usually aggregate in tissues and the specific arrangements of different tissues form organs.

In the invention "induced pluripotent cells" commonly abbreviated as iPS cells or iPSCs refers a type of pluripotent stem cell artificially derived from a non-pluripotent cell, typically an adult somatic cell, by inducing a "forced" expression of specific genes.

Induced pluripotent stem cells (iPS cells) are similar to natural pluripotent stem cells, such as embryonic stem (ES) cells, in many respects, such as the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

One of the unexpected observations made by the Inventors is that heterogous extract can synergize with iPS inducing genes to dedifferentiate differentiated cells. In other words, *Xenopus* extract, with iPS inducing genes, can act to dedifferentiate differentiated cells originating from multicellular organisms different from *Xenopus*.

Mutatis mutandis, mouse egg extracts could synergize with iPS inducing genes to dedifferentiate, for instance *Xenopus* differentiated cells.

All the combinations are possible, and the skilled person, without undue burden could easily choose the extract which is easier for him to carry out the method according to the invention.

Stem cells are primal undifferentiated cells that retain the ability to divide and can differentiate into other cell types. Totipotent stem cells can differentiate into embryonic and extra-embryonic cell types. Pluripotent stem cells originate from totipotent cells and can give rise to progeny that are derivatives of the three embryonic germ layers, mesoderm, ectoderm and endoderm.

Somatic cells are any cells other than oocytes and spermatozoids.

"Somatic differentiated cells" are somatic cells that are specialized in a particular function and that do not maintain the ability to generate other kinds of cells or to revert back to a less differentiated state.

The differentiated somatic cells may particularly originate from any kind of tissue of the organism, such as skin, intestine, liver, blood, muscle, etc.

To improve the entrance of the female germinal cell extract into the cells, the cell membrane is be permeabilized. The permeabilization of the cell membrane is achieved by the techniques well known in the art, such as the use of a chemical agent or a mild detergent, such as digitonine, Nonidet™ P40 (4-Nonylphenyl-polyethylene glycol; NP40), Triton® X100 (4-(1,1,3,3-Tetramethylbutyl)phenylpolyethylene glycol, t-Octylphenoxypolyethoxyethanol, Polyethylene glycol tent-octylphenyl ether), sodium deoxycholate (DOC), Triton® N101 (Polyoxyethylene branched nonylcyclohexyl ether), Brij® 96 (polyoxyethylene 10 oleoyl ether), or an enzyme that can make small holes in the cell membrane, as lysolecithin, or via a mechanical process which can at least partly open the cell membrane, for example pipetting.

Preferably, nucleus of the first cell, or the first cell comprising said nucleus are lightly permeabilized.

"Lightly permeabilization" is obtained for example by using low concentrations of detergent like NP40, Triton® X100, DOC, Triton® N101, Brij® 96, Lysolecithin, digitonin.

In one advantageous embodiment, the invention relates to the use as defined above, wherein said iPS cell is obtained by allowing the expression, in a somatic differentiated cell, of with at least an Oct family member protein and a Sox family member protein, along with at least one other factor chosen among a Klf family member protein, a Myc family member protein, the Nanog member protein and the LIN28 member.

In one advantageous embodiment, the invention relates to the use as defined above wherein said iPS cell is obtained by transfecting a somatic differentiated cell with genes coding for at least an Oct family member protein and a Sox family member protein, along with at least one other factor chosen among a Klf family member protein, a Myc family member protein, the Nanog member protein and the LIN28 member.

In one advantageous embodiment, the invention relates to the use as defined above, wherein said iPS cell is obtained by allowing the expression, in a somatic differentiated cell, of with at least an Oct family member protein and a Sox family member protein, along with
  either a Klf family member protein and a Myc family member protein,
  or the Nanog member protein and the LIN28 member.

In one advantageous embodiment, the invention relates to the use as defined above wherein said iPS cell is obtained by transfecting a somatic differentiated cell with genes coding for at least an Oct family member protein and a Sox family member protein, along with:
  either a Klf family member protein and a Myc family member protein,
  or the Nanog member protein and the LIN28 member.

In one another advantageous embodiment, the invention relates to the use as defined above, wherein said Oct family member protein is either the Oct3 or the Oct4 protein.

In one another advantageous embodiment, the invention relates to the use as defined above, wherein said Sox family member protein is the Sox2 protein.

In one other advantageous embodiment, the invention relates to the use as defined above, wherein said iPS cell is obtained by allowing the expression, in a somatic differentiated cell, of at least Oct4 protein and a Sox2 protein, along with at least one other factor chosen among a Klf family member protein, a Myc family member protein, a Nanog member protein and a LIN28 family member protein.

In one advantageous embodiment, the invention relates to the use as defined above wherein said iPS cell is obtained by transfecting a somatic differentiated cell with genes coding for at least an Oct4 protein and a Sox 2 protein, along with at least one other factor chosen among a Klf family member protein, a Myc family member protein, a Nanog member protein and a LIN28 family member protein.

The Inventors have demonstrated that the following minimal combination of genes:
  Oct4, Sox2 and a Klf family member protein,
  Oct4, Sox2 and a Myc family member protein
  Oct4, Sox2 and a Nanog member protein, and
  Oct4, Sox2 and a LIN28 family member protein,
  in combination with the extract mentioned above, are able to enhance the nuclear transfer and cloning with respect to the genes only or the extract only.

In one another advantageous embodiment, the invention relates to the use as defined above, wherein said Klf family member protein is the Klf4 protein.

In one another advantageous embodiment, the invention relates to the use as defined above, wherein said Myc family member protein is the c-Myc protein.

In still another advantageous embodiment, the invention relates to the use as defined above, wherein said iPS cell is obtained by the contact of a somatic differentiated cell, with:
  either a first composition Oct4, Sox2, Klf4 and c-Myc proteins,
  or a second composition Oct4, Sox2, Nanog, and LIN28 proteins.

The above combinations of genes are the preferred ones.

The invention relates, in another advantageous embodiment, to the use of as defined above, wherein said extract is substantially devoid of any cytoplasmic membrane.

On the contrary to other cloning techniques, consisting of fragmentation (sonication, mechanical fragmentation . . . ) of egg from which the nucleus has been extracted, the extract according to the invention is devoid of any cytoplasmic membrane. However, the extract may contain nuclear membrane precursors (vesicles containing nuclear envelop membranes) that could be used in order to reconstitute a functional nucleus.

In still another advantageous embodiment, the invention relates to the use as defined above, wherein said extract comprises EGTA in a concentration from 0.1 mM to 10 mM, preferably from 0.5 mM to 6 mM, more preferably from 1 mM to 4 mM, in particular from 1 to 2 mM.

In one embodiment, the invention relates to the use as defined above, wherein said isolated extract of female germinal cells, or isolated extract of eggs, are non-human cells.

The invention also relates to a composition comprising:
  at least one permeabilized nucleus of a first cell, or at least one permeabilized first cell comprising said nucleus
  said first cell originating from a multicellular organism, said first cell being an induced pluripotent stem cell, i.e. iPS cell, and
  a, possibly isolated, extract of female germinal cells, or of eggs, of a multicellular organism, said eggs being blocked in the metaphase II of meiosis, said extract comprising EGTA.

The nuclei can be extracted from the cells by the techniques well known in the art, such as cell breakage by incubation in a hypotonic buffer, use of a dounce homogeneizer or a potter homogeneizer or an isotonic buffer containing sucrose, glycerol or similar stabilizing agent and use of a potter homogeneizer or dounce homogeneizer able to open or disrupt the cell membrane.

The nuclei are either used directly or stored in specific conditions to maintain their integrity, such as storage at −20° C., −80° C. or in liquid nitrogen in conditions known to be used to store oocytes or early embryos.

In one advantageous embodiment, the invention relates to the composition as defined above, wherein said iPS cell is obtained by the contact of a somatic differentiated cell, with at least:
  an Oct family member protein and a Sox family member protein, and
  either a Klf family member protein and a Myc family member protein,
  or the Nanog member protein and the LIN28 member.

In one advantageous embodiment, the invention relates to a composition as defined above wherein said composition comprises:
  at least one permeabilized nucleus of a first cell, or at least one permeabilized first cell comprising said nucleus said first cell originating from a multicellular organism, said first cell, being an induced pluripotent stem cell, i.e. iPS cell, said iPS cell expressing a combination of genes coding for at least:
- an Oct family member protein and a Sox family member protein, and
- either a Klf family member protein and a Myc family member protein,
- or the Nanog member protein and the LIN28 member. and
- an isolated extract of female germinal cells, or of eggs, of a multicellular organism, said eggs being blocked in the metaphase II of meiosis, said extract comprising EGTA.

In one another advantageous embodiment, the invention relates to the composition as defined above, wherein said Oct family member protein is either the Oct3 or the Oct4 protein.

In one another advantageous embodiment, the invention relates to the composition as defined above, wherein said Sox family member protein is the Sox2 protein.

In one another advantageous embodiment, the invention relates to the composition as defined above, wherein said Klf family member protein is the Klf4 protein.

In one another advantageous embodiment, the invention relates to the composition as defined above, wherein said Myc family member protein is the c-Myc protein.

In still another advantageous embodiment, the invention relates to the composition as defined above, wherein said iPS cell is obtained by the contact of a somatic differentiated cell, with the four proteins Oct4, Sox2, Klf4 and c-Myc proteins, or with the four proteins Oct4, Sox2, Nanog, and LIN28 proteins.

In one another advantageous embodiment, the invention relates to the composition as defined above, wherein said iPS cell is obtained by transfecting a somatic differentiated cell with genes coding the four proteins Oct4, Sox2, Klf4 and c-Myc proteins, or the four proteins Oct4, Sox2, Nanog, and LIN28 proteins.

Both of said four proteins have similar effects regarding their synergistic effect when used with the extract as defined in the invention.

The invention relates, in another advantageous embodiment, to the composition of as defined above, wherein said extract said extract is substantially devoid of any lipid membrane.

In still another advantageous embodiment, the invention relates to the composition as defined above, wherein said extract comprise EGTA in a concentration from 0.1 mM to 10 mM, preferably from 0.5 mM to 6 mM, more preferably from 1 mM to 4 mM, in particular from 1 to 2 mM.

In one advantageous embodiment, the invention relates to a composition as defined above, wherein said female germinal cells are vertebrate female germinal cells, preferably chosen among mammals, in particular humans, birds, reptiles and amphibians.

The techniques for obtaining egg, or female germinal cells, from the above vertebrate are current veterinary techniques well known in the art.

In one another advantageous embodiment, the invention relates to a composition as defined above, wherein said female germinal cells are *Xenopus* cells.

The *Xenopus* eggs are obtained as disclosed in Menut et al. 1999.

In one embodiment, the invention relates to a composition as defined above, wherein said isolated extract of female germinal cells, or isolated extract of eggs, are non-human cells.

The invention also relates to a method for producing pluripotent stem cells, comprising a step of contacting at least one permeabilized nucleus of a first cell, or at least one permeabilized first cell comprising said nucleus, said first cell originating from a multicellular organism, said first cell, being an induced pluripotent stem cell, i.e. iPS cell, with an (isolated) extract of female germinal cells, or of eggs, of multicellular organism, said eggs being blocked in the metaphase II of meiosis, said extract comprising EGTA.

The invention also relates to a method for producing pluripotent stem cells, comprising a step of contacting at least one permeabilized nucleus of a first cell, or at least one permeabilized first cell comprising said nucleus, said first cell originating from a multicellular organism, said first cell being an induced pluripotent stem cell, i.e. iPS cell, with an extract of female germinal cells, or of eggs, of multicellular organism, said eggs being blocked in the metaphase II of meiosis, said extract comprising EGTA, possibly provided that said method is not a process for cloning human beings.

The term "contacting" means that the cells, or nuclei, and the female germinal extract are present together in suitable conditions, in order to allow the diffusion of the molecules contained in the female germinal extract into said cells or nuclei. The contact is carried out preferably at a temperature preferably comprised from 20° C. to 23° C., and preferentially for at least 10 minutes, more preferably at least 20 minutes, more preferably at least 30 min.

According to the method mentioned above, permeabilized nuclei of a differentiated cells, or permeabilized differentiated cells, after a contact with the extract of female germinal cells, or of eggs, of multicellular organism, said eggs being blocked in the metaphase II of meiosis, said extract comprising EGTA, have acquire, or re-acquire all the features of a pluripotent stem cell.

In one advantageous embodiment, the invention relates to the method as defined above, wherein said iPS cell is obtained by the contact of a somatic differentiated cell, with at least:
- an Oct family member protein and a Sox family member protein, and
- either a Klf family member protein and a Myc family member protein,
- or the Nanog family member protein and the LIN28 family member protein.

In one advantageous embodiment, the invention relates to the method as defined above, wherein said iPS cell is obtained by transfecting a somatic differentiated cell, with genes coding at least:
- an Oct family member protein and a Sox family member protein, and
- either a Klf family member protein and a Myc family member protein,
- or the Nanog family member protein and the LIN28 family member protein.

In one advantageous embodiment, the invention relates to the method as defined above, wherein said Oct family member protein is either the Oct3 or the Oct4 protein.

In one advantageous embodiment, the invention relates to the method as defined above, wherein said Sox family member protein is the Sox2 protein.

In one advantageous embodiment, the invention relates to the method as defined above, wherein said Klf family member protein is the Klf4 protein.

In one advantageous embodiment, the invention relates to the method as defined above, wherein said Myc family member protein is the c-Myc protein.

Thus, in the case of the permeabilized cells, if the cells are maintained in an appropriate culture medium, preferably a culture medium used for maintaining ES cells, said cells will harbour similar features with respect to the ES cells, after the contact with the extract, and the re-expression of the above genes, i.e. Oct4, Sox2, Klf4 and c-Myc proteins or Oct4, Sox2, Nanog, and LIN28 proteins.

In one advantageous embodiment, the invention relates the method as defined above wherein, in the first step of transfecting a differentiated somatic cell with genes coding for at least:
 either a first combination of Oct4, Sox2, Klf4 and c-Myc proteins,
 or a second combination of Oct4, Sox2, Nanog, and LIN28 proteins,
 the first combination or the second combination comprises respectively at least nucleic acid coding for Oct4, Sox2, Klf4 and c-Myc proteins, or Oct4, Sox2, Nanog, and LIN28 proteins.

In one advantageous embodiment, the invention relates to the method defined above, said method comprising
 a step of contacting a differentiated somatic cell with
  either a first composition Oct4, Sox2, Klf4 and c-Myc proteins,
  or a second composition Oct4, Sox2, Nanog, and LIN28 proteins,
 to obtain a first cell which is an iPS cell,
 a step of permeabilizing said first cell obtained in the previous step, to obtain permebilised iPS cells and
 a step of contacting said permeabilized iPS cell with an (isolated) extract of female germinal cells, or eggs, of multicellular organism, said eggs being blocked in the metaphase II of meiosis, said extract comprising EGTA.

In one advantageous embodiment, the invention relates to the method defined above, said method comprising
 a step of transfecting a differentiated somatic cell with genes coding for
  either a first combination of Oct4, Sox2, Klf4 and c-Myc proteins,
  or a second combination Oct4, Sox2, Nanog, and LIN28 proteins,
 to obtain a first cell which is an iPS cell,
 a step of permeabilizing said first cell obtained in the previous step, to obtain permebilised iPS cells and
 a step of contating said permeabilized iPS cell with an isolated extract of female germinal cells, or of eggs, of multicellular organism, said eggs being blocked in the metaphase II of meiosis, said extract comprising EGTA.

In one advantageous embodiment, the invention relates to the method defined above, wherein said female germinal cells are vertebrate female germinal cells, preferably chosen among mammals, in particular humans, birds, reptiles and amphibians, preferably said germinal cells are *Xenopus* cells.

In one embodiment, the invention relates to the method as defined above, wherein said isolated extract of female germinal cells, or said isolated extract of eggs, are non-human cells.

The invention also relates to the pluripotent stem cells liable to be obtained by the process according to the method previously defined.

The Inventors have demonstrated that the cells obtained by the process according to the invention harbour an epigenetic pattern that differs from the pattern of the natural stem cells.

In one advantageous embodiment, the invention relates to the method defined above, wherein, in the step of contacting a differentiated somatic cell with
 either a first composition Oct4, Sox2, Klf4 and c-Myc proteins,
 or a second composition Oct4, Sox2, Nanog, and LIN28 proteins,
 the first composition or the second composition comprise respectively at least a nucleic acid coding for Oct4, Sox2, Klf4 and c-Myc proteins, or Oct4, Sox2, Nanog, and LIN28 proteins.

In one advantageous embodiment, the invention relates to the method defined above, wherein said at least nucleic acid coding for Oct4, Sox2, Klf4 and c-Myc proteins, or Oct4, Sox2, Nanog, and LIN28 proteins is comprised in at least one viral vector, preferably in at least one retroviral vector, in particular in at least one integrative retroviral vector or a lentiviral vector.

In one advantageous embodiment, the invention relates to the method defined above, wherein said at least one integrative retroviral vector is integrated into the genome of said differentiated somatic cell.

In one advantageous embodiment, the invention relates to the method defined above, said method further comprising a step of culturing the cells obtained in the previous step in a medium allowing maintaining the pluripotency of said pluripotent stem cells.

"Medium allowing maintaining the pluripotency of said pluripotent stem cells" is a medium containing nutriments, growth factors, hormones . . . that allows the cellular division of the undifferentiated cells.

For instance, ES cells are grown at 37° C./5% CO2/95% humidity in dishes coated with a feeder layer of mitotically inactivated primary mouse embryonic fibroblasts, in a DMEM (high glucose, Gibco 41966-052, store in fridge) minimal medium supplemented before use with:
 15% (v/v) FCS (serum from newborn calf, liquid, tested for ES culture, store aliquots at −20° C.)
 1/100 (v/v) L-glutamine (200 mM: Gibco 25030-024, store aliquots at −20° C.), stable in solution for 10 d only
 1/100 (v/v) non-essential amino acids (Gibco 11140-035, store aliquots in fridge)
 1/100 (v/v) pen/strep (Gibco 15140-122, store aliquots at −20° C.)
 1/500 (v/v) 2-mercaptoethanol (Gibco 31350-010, 0.1 mM final conc., store aliquots in fridge)
 1/10,000 (v/v) LIF (leukemia Inhibiting Factor) ("ES-GRO" from Chemicon, No. ESG1107, 1000 U/ml final conc. or less (depending on properties of respective cell line), make up 1/100 dilution in DMEM with 10% (v/v) or so serum to be further diluted by 1/100 to achieve the working conc., store at −20° C.).

The skilled person can easily adapt the above protocol.

In one advantageous embodiment, the invention relates to the method as defined above, wherein said extract is substantially devoid of any plasma membrane.

In one advantageous embodiment, the invention relates to the method as defined above, wherein said extract comprise EGTA in a concentration from 0.1 mM to 10 mM, preferably from 0.5 mM to 6 mM, more preferably from 1 mM to 4 mM, in particular from 1 to 2 mM.

The invention also relates to a method for cloning animals, preferably mammals, comprising
- a step of producing pluripotent stem cell as defined in the method according to the previous definitions
- a step of transferring the nucleus of said pluripotent stem cell into an enucleated egg of an animal of the same species as the species from which said pluripotent stem cell derives, to obtain an allo-nucleated egg, and
- a step of transferring said allo-nucleated egg in a pseudopregnant female of the same species as the species from which said pluripotent stem cell derives.

In this advantageous embodiment, the method for cloning animal according to the invention is as follows:
- differentiated cells are dedifferentiated by expressing the genes as mentioned above.
- nuclei of said cells are extracted, slightly permeabilized, and exposed to the isolated extract of female germinal cells, or of eggs, of multicellular organism, said eggs being blocked in the metaphase II of meiosis, said extract comprising EGTA,
- the nuclei are then optionally washed with PBS,
- the nuclei are transferred in an enucleated eggs.

The enucleated eggs are obtained by removing the nucleus of the egg by techniques well known in the art. Thus, the nuclei treated by the extracts according to the invention are micro injected in said enucleated eggs. Preferably, the nuclei treated according to the invention are micro injected in enucleated eggs of the same species. For instance a mouse nucleus is injected in a mouse enucleated egg. The newly obtained nucleated egg is then called allo-nucleated egg.

However, it is possible to micro inject the nuclei into an enucleated egg of a different species witch is not completely different. For instance a mouse nucleus is injected in a rat enucleated egg, and vice versa. The newly obtained nucleated egg is then called hetero-nucleated egg.
- the newly obtained nucleated egg (hetero or allo nucleated egg) is thus transferred into the uterus of a pseudopregnant female of the same species as the species from which the enucleated egg derives.

Therefore, if the enucleated egg is obtained from a mouse, the pseudo pregnant female will be a mice. If the enucleated egg is obtained from a rat, the pseudo pregnant female will be a rat.

Progeny obtained from said pseudo pregnant female will be then clones of the animal which have given the nuclei treated according to the invention.

The invention also relates to a method for cloning animals, preferably mammals, comprising
- a step of producing pluripotent stem cells as defined in the method as defined above,
- a step of transferring the nucleus of said pluripotent stem cells in an enucleated egg of an animal of the same species as the species from which said pluripotent stem cells derive, to obtain an allo-nucleated egg,
preferably, provided that said method is not a process for cloning human beings.

The invention also relates to animals liable to be obtained by the process according to the method previously defined.

In the context of the invention, the term "cloning" means obtaining an entire animal, or embryo of said animal, from the nuclei of a donor cell.

The nuclei of the donor cells can be activated to trigger the S-phase of the cell cycle, in order to initiate the first divisions of the early embryonic development. The activation may be achieved by the techniques well known in the art.

The egg extract can be partially or totally removed, particularly by washing the nuclei or the cells containing said nuclei, for example by several washings in Phosphate Buffer Saline (PBS).

The nuclei are introduced into an enucleated egg, according to the techniques well known in the art, such as microinjection.

For each enucleated egg, one nucleus or one donor cell is introduced.

The enucleated egg preferentially originates from the same species as the nuclei. The enucleated egg is obtained by techniques well known in the art.

The enucleated egg containing the nuclei can then be transferred into a female breeder, so as to perform its early-embryonic, embryonic and fetal development.

The cells originate from different tissues of an organism can particularly be chosen among cells originating from any kind of tissue, such as skin, intestine, liver, blood, muscle, etc.

The invention also relates to a method for obtaining cells, cellular lines or tissues of pluricellular organisms, particularly vertebrates, at the desired stage of differentiation, comprising:
- a step of producing pluripotent stem cells as defined in the method as defined above,
- a step of culturing the pluripotent stem cells in appropriate conditions to obtain cells, cellular lines or tissues, at the desired stage of differentiation.

The resulting multipotent or totipotent stem cells can be cultured under appropriate conditions to maintain said cells in an undifferentiated state.

The skilled person knows from his general knowledge what are the preferred growth factors, hormones, medium, and stimulations . . . to achieve a specific differentiation toward a specific type of cells, to obtain cells or organs at a different stage, preferably in vitro.

The invention also relates to cellular lines or tissues of pluricellular organisms, particularly vertebrates, at the desired stage of differentiation, liable to be obtained by the process according to the method previously defined.

FIGURES

FIGS. 1A-D show that M phase *Xenopus* egg extracts improve the efficiency of nuclear transfer and iPS cells production from mammalian fibroblasts.

FIG. 1A is a schematic representation of nuclear transfer experiments using MEFs exposed to M phase *Xenopus* egg extracts (M phase).

FIG. 1B is a graph re presenting the percentage of 2 cells (A), 4-8 cells (B) morulas (C) and (blastocystes) resulting from nuclear transfer of MEFs (open square), MEFs exposed to M phase (M-Extract; Black square) and MEFs exposed to interphase (I-Extract; black circles) *Xenopus* egg extracts and normalized to the number of 2 cell-embryos. As control, ES cells are represented (black diamond).

FIG. 1C is a schematic representation of iPS cell generation from OCT4-GFP positive MEFs by ectopic expression of Oct4/Klf4/Sox2/c-Myc (OKSM) followed, or not (mock), by exposure to M phase *Xenopus* egg extracts.

FIG. 1D represents the number of OCT4-GFP positive colonies relative to non-permeabilized cells. The effect of exposure to M phase egg extracts on the efficiency of iPS cell production was assessed by measuring the production of OCT4-GFP positive colonies after exposure to M phase egg extracts (M phase alone, A), OKSM over-expression (OKSM alone, B) and OKSM over-expression followed by exposure to buffer alone (OKSM+mock; C) or to M phase egg extracts (OKSM+M phase; D), in three fully independent experiments. Error bars represent s.e.m. (n=3).

FIGS. 2A-U show the characterization of the pluripotency of iPS cells obtained by OKSM overexpression followed by exposure to M phase *Xenopus* egg extracts FIGS. 2A-F represent the alkaline phosphatase expression in mock-treated MEFs (FIG. 2A and FIG. 2D), ES cells (FIG. 2B and FIG. 2E) and iPS cells induced by OKSM over-expression and exposure to M phase egg extracts (M phase iPS; FIG. 2C and FIG. 2F). FIGS. 2D-F represent respectively higher magnification of FIGS. 2A-C.

FIGS. 2G-J represents the morphology (FIG. 2G, FIG. 2I) and GFP expression (FIG. 2H, FIG. 2J) in M phase iPS cells generated from OCT4-GFP MEFs. FIGS. 2I-J-F represent respectively higher magnification of FIGS. 2G-H.

FIGS. 2K-S represent the expression of pluripotency markers assessed by immunofluorescence in M phase iPS cells: OCT4 (FIG. 2K), Nanog (FIG. 2N) and SSEA1 (FIG. 2Q) co-localized with GFP whose expression was driven by the promoter of OCT4 (FIG. 2L, FIG. 2O and FIG. 2R). DNA is labelled with DAPI (FIG. 2M, FIG. 2P and FIG. 2S).

FIG. 2T represents the expression of Oct4 measured by quantitative RT-PCR in MEFs (first column), ES cells (second column) and two M phase iPS clones (M/iPS; two last columns). Error bars represent s.e.m. (n=3). Y-axis represents the expression of mRNA relative to ES cells.

FIG. 2U represents the expression of Nanog measured by quantitative RT-PCR in MEFs (first column), ES cells (second column) and two M phase iPS clones (M/iPS; two last columns). Error bars represent s.e.m. (n=3). Y-axis represents the expression of mRNA relative to ES cells.

FIGS. 3A-L show the developmental potential of M phase-iPS cells

FIGS. 3A-F represent the differentiation of embryoid bodies (EB) was induced by retinoic acid as described in Material and Methods. EB formation was accompanied by loss of GFP expression.

FIGS. 3C and F correspond respectively to the higher magnification of FIGS. 3B and 3E.

FIGS. 3G-I represents chimeric mice produced using M phase iPS cells. Two different M phase iPS clones produced viable chimeras after injection into CD1 blastocysts.

Figure 3J:
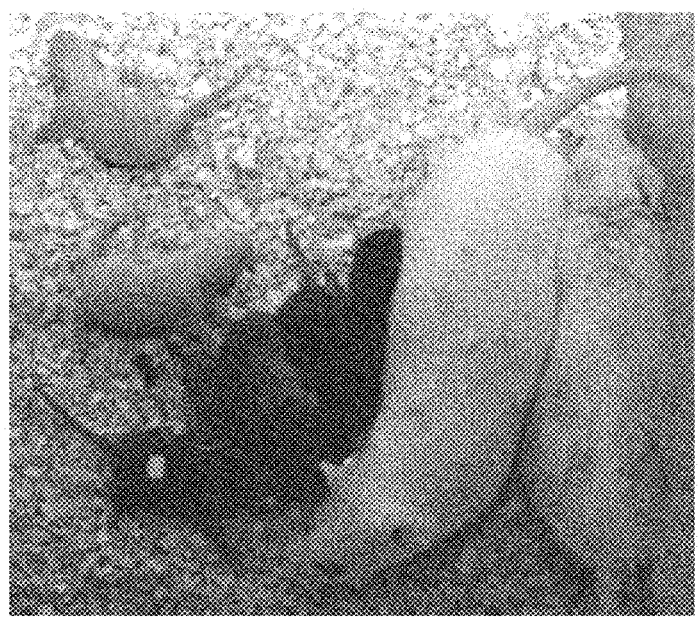
FIG. 3A represents a differentiating embryoid body.
FIG. 3D represents the GFP expression of the differentiating embryoid body of FIG. 3A.
FIG. 3B represents differentiated embryoid bodies.
FIG. 3E represents the GFP expression of differentiated embryoid bodies of FIG. 3B.

FIG. 3J shows the black color of the F1 pups (from the (B6xJF1) genotype) and demonstrates germline transmission.

Figure 4N:
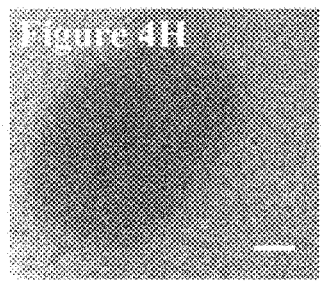
Figure 4N:
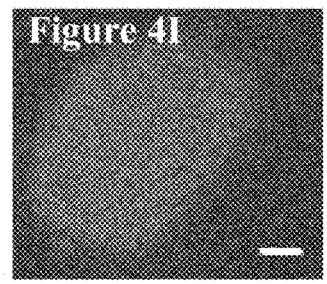
Figure 4N:
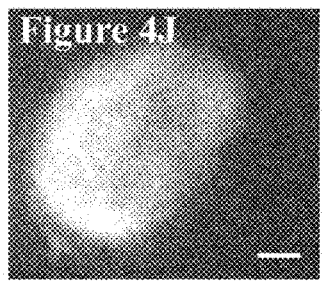
Figure 4N:
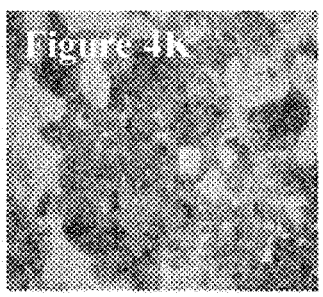
Figure 4N:
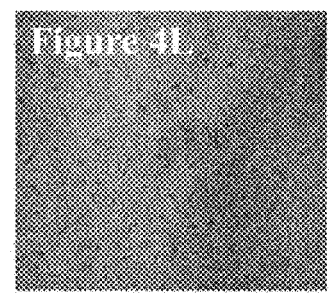
Figure 4N:
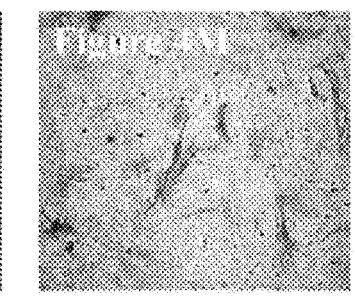
Figure 4N:
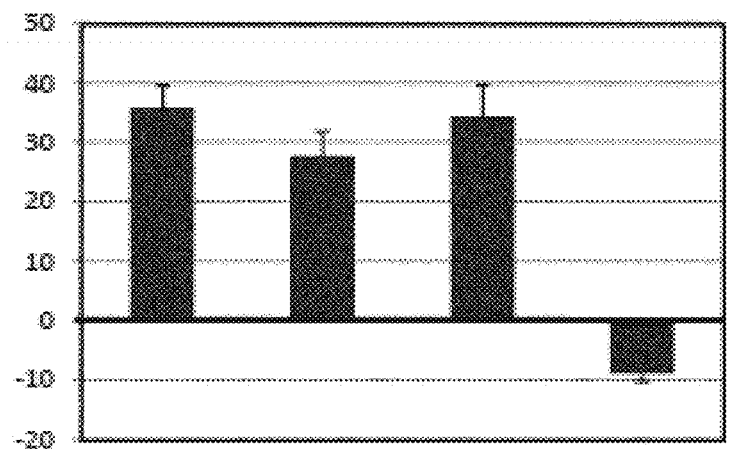

FIG. 4A-N show the reprogramming of permeabilized MEFs induced by M phase *Xenopus* egg extracts.

FIG. 4A represents a curve showing the proliferation rate of M phase extract-treated MEFs (circles) compared to mock-treated MEFs (squares) at different days (D) after exposure. Error bars represent s.e.m. (n=4). Y-axis represents the total cell number×$10^5$.

FIGS. 4B-G represent the morphology of colonies formed following treatment of MEFs with M phase *Xenopus* egg extracts (phase contrast).

FIGS. 4B-E represent respectively different colonies induced by M phase extract treatment at low magnification (×34).

FIGS. 4F and 4G represent the morphology of colonies at higher magnification.

FIG. 4H-J represent the induction of OCT4 positive colonies following exposure to M phase egg extracts of wild type MEFs (immunofluorescence analysis); Scale bar, 100 μm. FIG. 4J represents the induction of GFP expression in OCT4-GFP MEFs after incubation with M phase extracts; FIG. 4H represent the phase contrast; FIG. 4I represent the DNA labelling (DAPI); scale bar, 50 μm.

FIGS. 4K-M represent the Induction of alkaline phosphatase activity in ES cells (FIG. 4K), MEFs (FIG. 4L) and in MEFs after exposure to M phase egg extracts (FIG. 4M).

FIG. 4 N represents the induction of the expression of pluripotency markers (Oct4, Nanog and Rex1, first to thirds column respectively) and downregulation of Zfpm2 (a differentiation marker; fourth column) after incubation with M phase egg extracts. Quantitative RT PCR was performed using M phase extract- and mock-treated MEFs. Error bars represent s.e.m. (n=3).

Figure 5P:
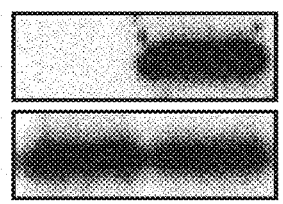
Figure 5Q:
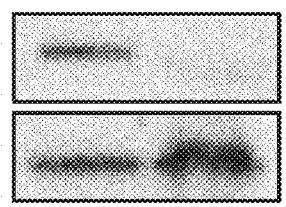
Figure 5R:
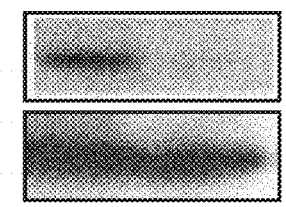
Figure 5S:
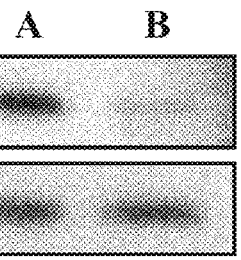
Figure 5T:
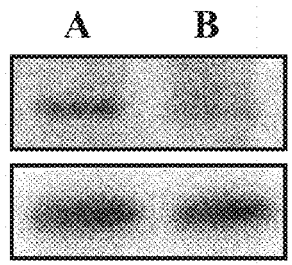
Figure 5U:
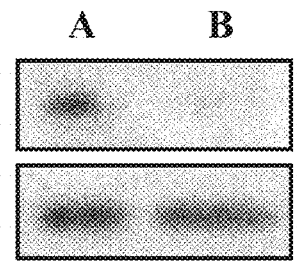
Figure 5V:
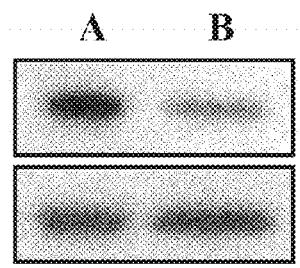
Figure 5W:
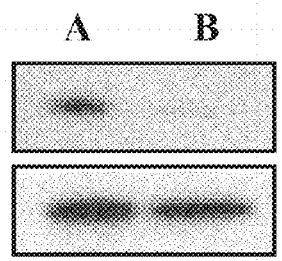
Figure 5X:
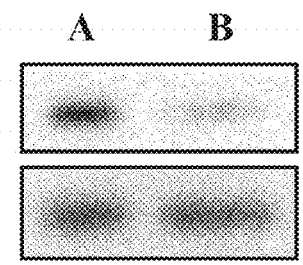
Figure 5Y:
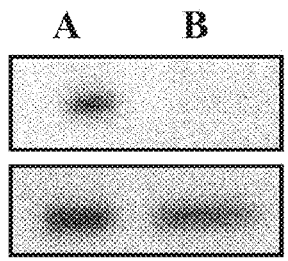
Figure 5Z:
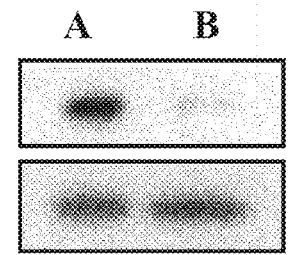
Figure 5A:
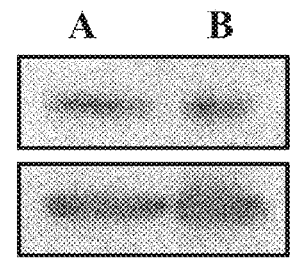
Figure 5A:
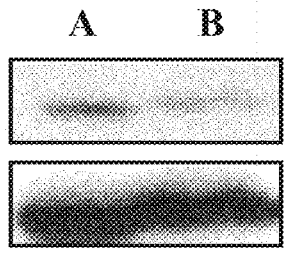

FIGS. 5A-AB show the remodeling of chromatin structure and acceleration of DNA replication in MEF nuclei incubated with M phase *Xenopus* egg extracts.

FIGS. 5A-D represent the morphology of MEF nuclei incubated for 40 min with buffer alone (FIG. 5C and FIG. 5D) or with M phase egg extracts (FIG. 5A and FIG. 5B). Nuclei were stained with DAPI (scale bar=10 μm).

FIGS. 5E-G represent the morphology of MEF nuclei treated with buffer alone (FIG. 5E) or M phase egg extracts at 40 min (FIG. 5F) or 60 min (FIG. 5G). Nuclei (stained with DAPI) show different degrees of chromatin compaction. Scale bar=10 μm.

FIGS. 5H-O represent the phosphorylation of histone H3 at Ser 10 (phospho H3) and loss of HP1-α bound to chromatin after exposure of MEF nuclei, or not (Mock), to M phase egg extracts. MEF nuclei were fixed and stained with the corresponding antibodies and DNA was stained with DAPI. Scale bar=10 μm.

FIG. 5H represents the DNA labelling (DAPI) of a mock treated MEF nucleus.

FIG. 5I represents the labelling with an anti phosphorylated histone H3 (Ser 10) (phospho H3) antibody of a mock treated MEF nucleus.

FIG. 5J represents the DNA labelling (DAPI) of a mock treated MEF nucleus.

FIG. 5K represents the labelling with an anti HP1-α antibody of a mock treated MEF nucleus.

FIG. 5L represents the DNA labelling (DAPI) of a M phase extract treated MEF nucleus.

FIG. 5M represents the labelling with an anti phosphorylated histone H3 (Ser 10) (phospho H3) antibody of a M phase extract treated MEF nucleus.

FIG. 5N represents the DNA labelling (DAPI) of a M phase extract treated MEF nucleus.

FIG. 5O represents the labelling with an anti HP1-α antibody of a M phase extract treated MEF nucleus.

FIGS. 5P-R represents the analysis of the expression of chromatin-bound phosphorylated histone H3 at Ser 10 (FIG. 5P, upper panel), Lamin B1 (FIG. 5Q, upper panel) and HP1-α (FIG. 5R, upper panel) in MEF nuclei after incubation, or not (A), with M phase egg extracts (B). Chromatin was collected by centrifugation after treatment as described in Example 2. Samples were analyzed by western blotting using the corresponding antibodies. Histone H3 was probed as loading control (FIGS. 5P, 5Q and 5R, lower panel.

FIGS. 5S-AB represents the analysis of histone modifications in MEF nuclei after incubation in M phase extracts (B) or not (A). Samples were analyzed by western blotting using the corresponding antibodies. Histone H3 was probed as loading control (lower panel of each of FIGS. 5S-AB).

Upper panel of FIG. 5S represents the blotting with anti acetyl histone H3 (aCH3) antibody.

Upper panel of FIG. 5T represents the blotting with anti acetyl lysine 9 histone H3 (H3K9) antibody.

Upper panel of FIG. 5U represents the blotting with anti acetyl lysine 8 histone H4 (H4K8) antibody.

Upper panel of FIG. 5V represents the blotting with anti H3K9me3 antibody.

Upper panel of FIG. 5W represents the blotting with anti H3K9me2 antibody.

Upper panel of FIG. 5X represents the blotting with anti H4K20me3 antibody.

Upper panel of FIG. 5Y represents the blotting with anti H3K4me3 antibody.

Upper panel of FIG. 5Z represents the blotting with anti H3K4me2 antibody.

Upper panel of FIG. 5AA represents the blotting with anti H3K27me3 antibody.

Upper panel of FIG. 5AB represents the blotting with anti histone variant H3.3 antibody.

FIG. 6: Pre-incubation with M phase *Xenopus* egg extracts accelerates the rate of DNA replication of MEF nuclei in interphasic egg extracts.

Figure 6A:
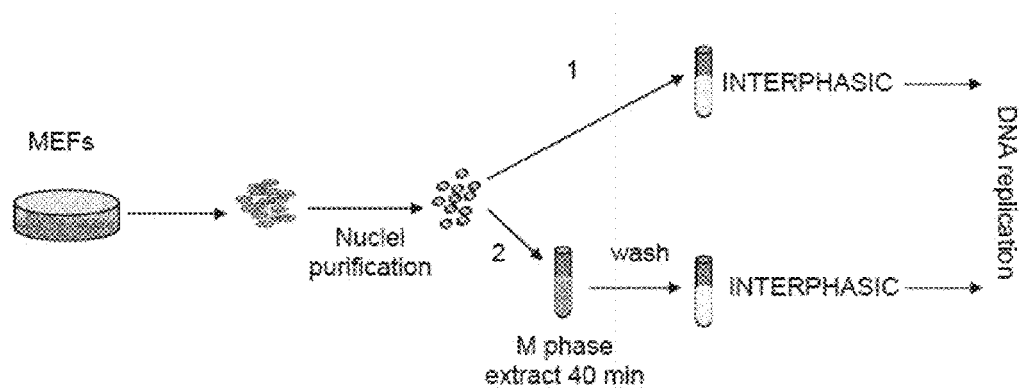

FIG. 6A is a schematic representation of the procedure used to evaluate DNA replication in MEF nuclei after incubation with *Xenopus* M phase and/or interphase egg extracts.

Figure 6B:
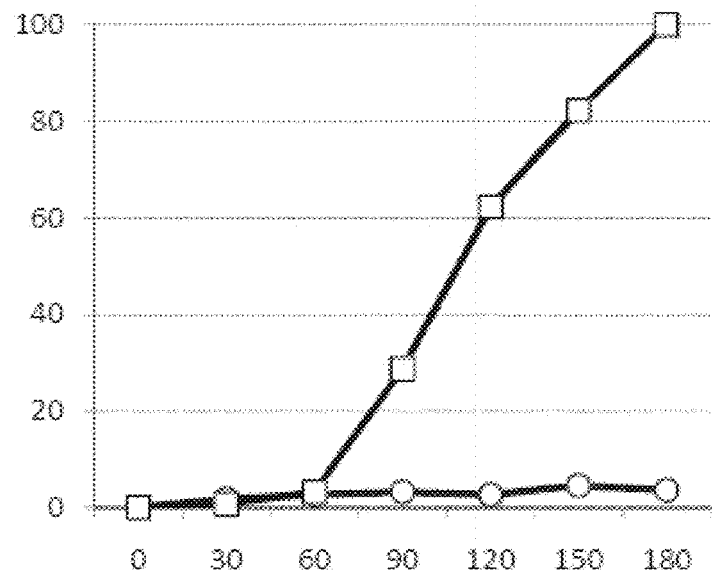

FIG. 6B represents the DNA replication of permeabilized MEF nuclei (line with circles) and *Xenopus* sperm nuclei (line with squares) in *Xenopus* interphase egg extracts. The percentage of DNA replication is relative to the total DNA input in the reaction (see Material and Methods of Example 2). Y-axis represents the % of DNA replication, and X-axis represents the incubation time in min.

Figure 6C:
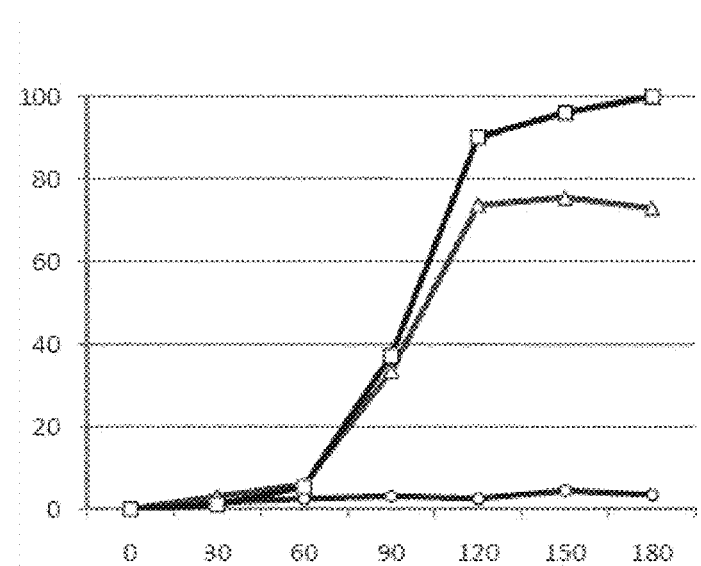

FIG. 6C shows that the pre-incubation of permeabilized MEF nuclei in M phase egg extracts (CSF; line with triangles) enables them to replicate DNA as efficiently as sperm nuclei in interphasic egg extracts (line with squares). As control, interphasic extract is shown (line with circles). Y-axis represents the % of DNA replication, and X-axis represents the incubation time in min.

Figure 7:
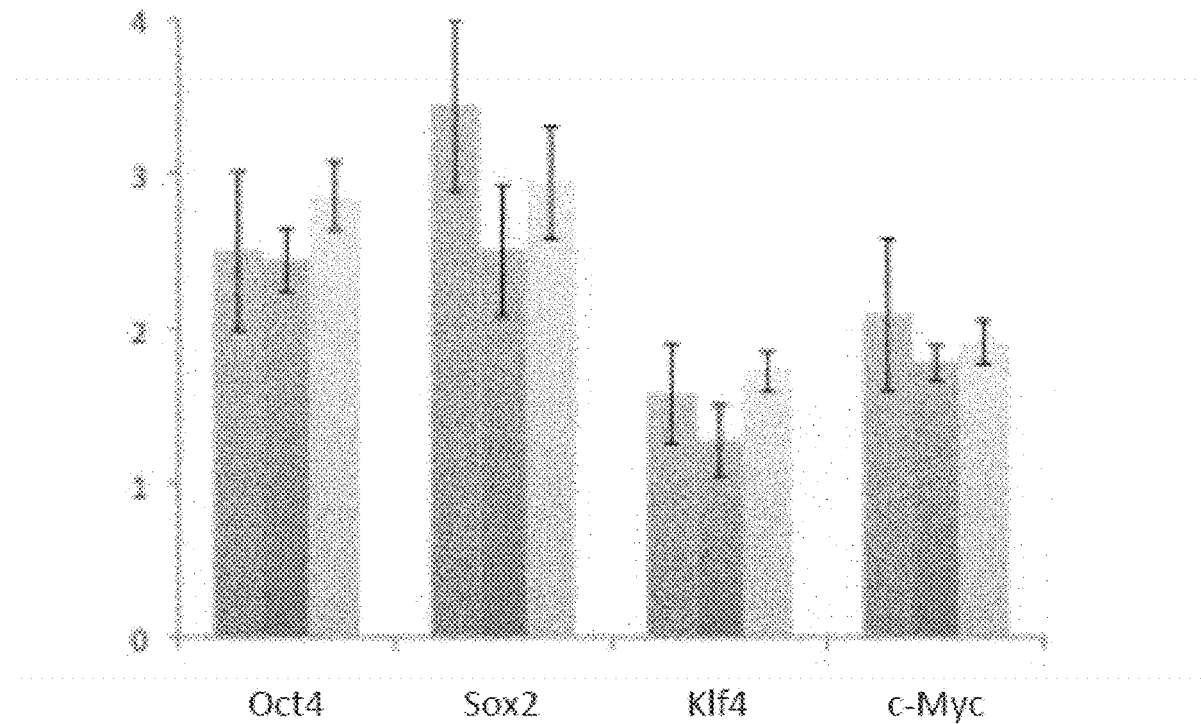

FIG. 7: Incubation with M phase *Xenopus* egg extracts does not affect the viral integration of the OKSM trangenes.

Viral integration of each transgene (Oct4, Sox2, Klf4 and c-Myc) in the different cell populations was assessed by quantitative PCR amplification. The different MEF populations were harvested 21 days after infection and their DNA extracted.

First bars (middle grey) correspond to infected, non-permeabilized cells (OKSM);

Second bars (dark grey) correspond to infected, streptolysin-O (SLO)-permeabilized and mock-treated cells (OKSM+SLO+buffer);

Third bars (light grey) corresponds to SLO-permeabilized and M phase extract-treated cells (OKSM+SLO+M phase extract).

Four independent experiments are shown and errors bars represent s.e.m. (n=4).

Y-axis represents the relative number of integrated transgenes, measured by Q-PCR.

Figure 8:
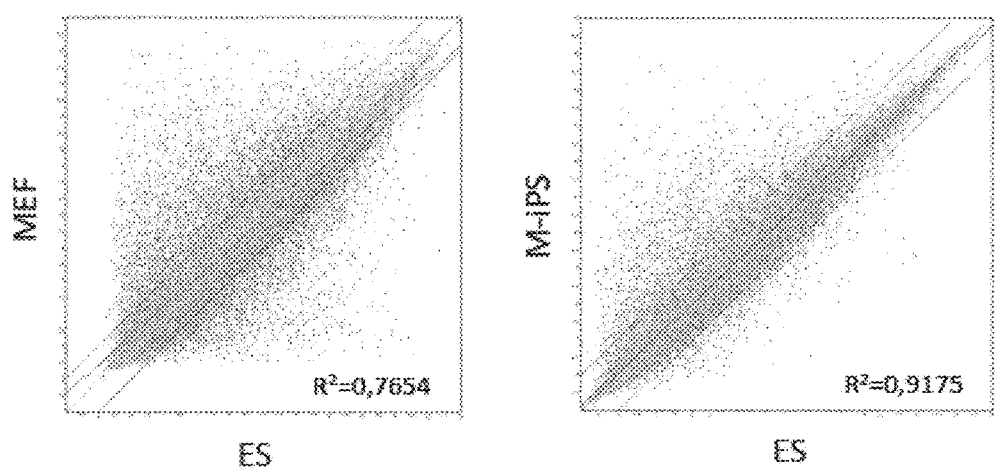

FIG. 8 represents Scatter plots with computation of the Pearson's correlation coefficient ($R^2$) showing the comparisons of global gene expression between ES cells and MEFs (left) and between ES and M-iPS cells (right). Lines indicate the differentially expressed genes between paired cell types.

Figure 9A:
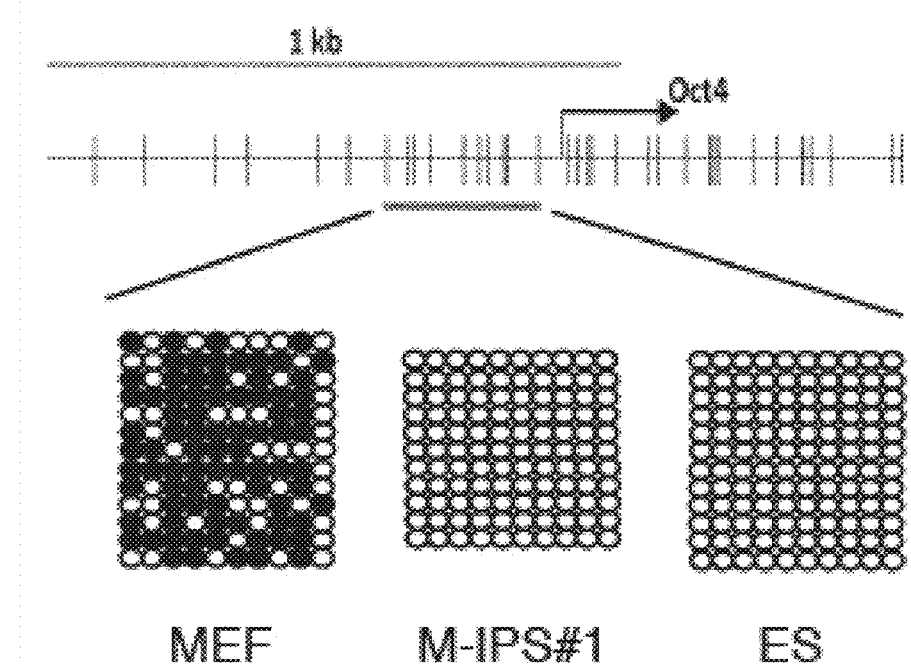

FIGS. 9A and B represent bisulfite sequencing of DNA from MEFs, ES cells and M-iPS cells. The amplified regions are indicated by a solid blue bar. Each horizontal row of circles represents the CpG dinucleotides of an individual molecule. Solid circles depict methylated CpGs, open circles unmethylated CpGs.

FIG. 9A represents the analysis of the promoter region of Oct4.

Figure 9B:
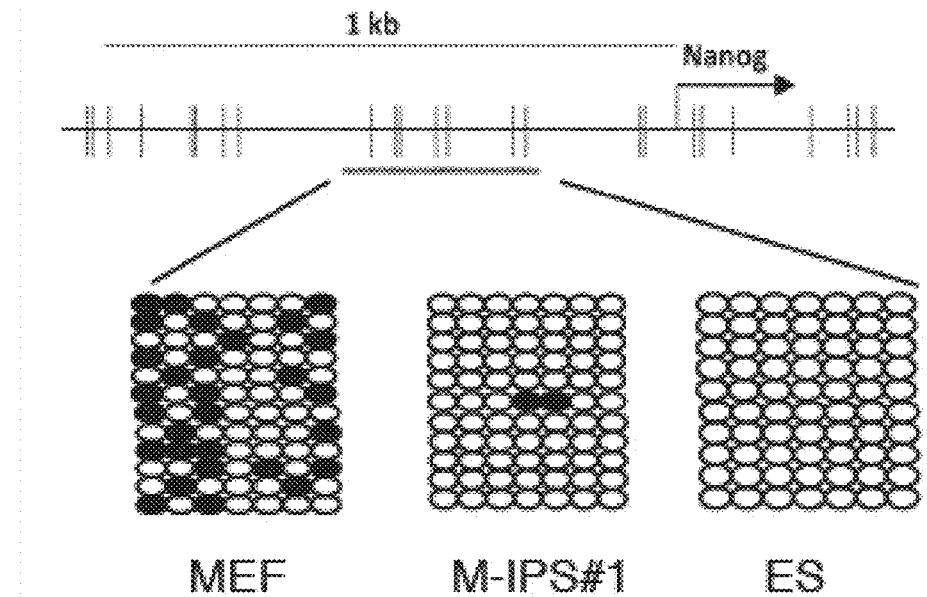

FIG. 9B represents the analysis of the promoter region of Nanog.

Figure 10:
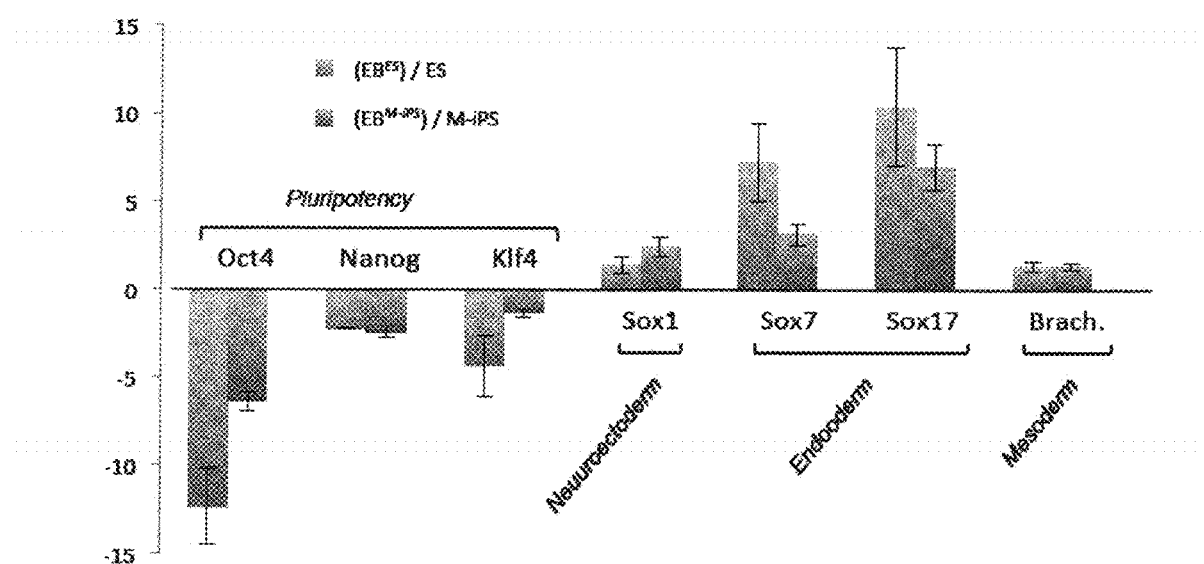

FIG. 10 represents the down-regulation of the pluripotency markers Oct4, Nanog and Klf4 and up-regulation of the differentiation markers Sox1, Sox7, Sox17 and Brachyury (Brach) upon EB differentiation. The analysis was performed by quantitative RT-PCR amplification of RNA from ES cells, ES-derived embryoid bodies ($EB^{ES}$), M-iPS and M-iPS derived embryoid bodies ($EB^{M-iPS}$) and normalized to the mean expression of Actin, HPRT and GAPDH. Histograms represent the ratio between the corresponding embryoid bodies and pluripotent cells (ES, blue bars or M-iPS cells, red bars) and their. Error bars represent s.e.m. (n=3). Y-axis represents the fold induction of mRNA relative to housekeeping genes.

Figure 11A:
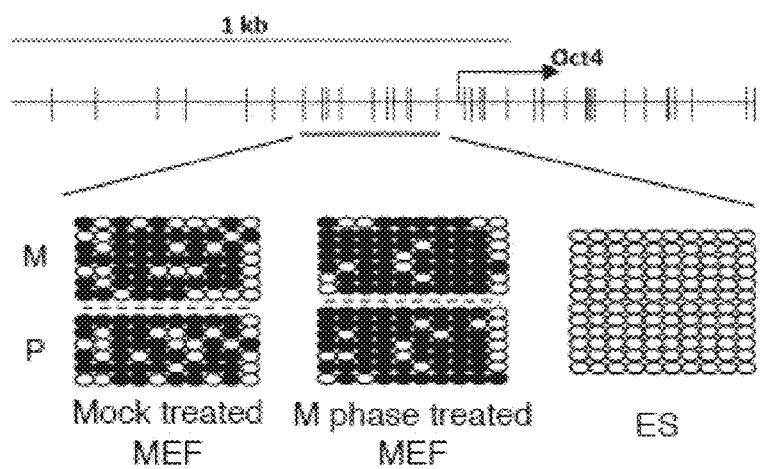
Figure 11B:
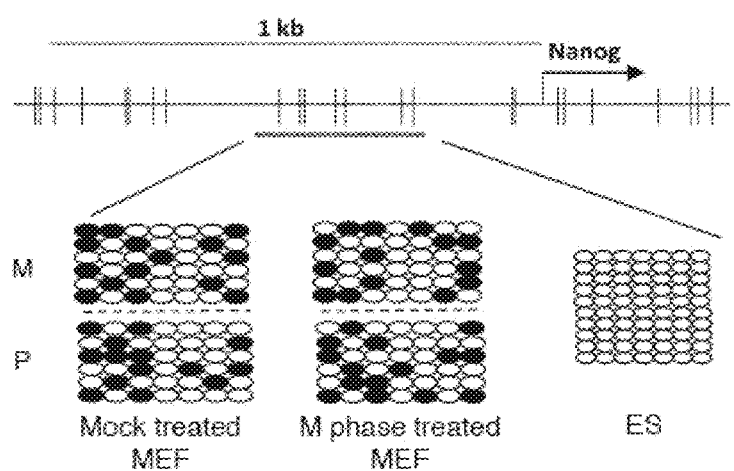
Figure 11C:
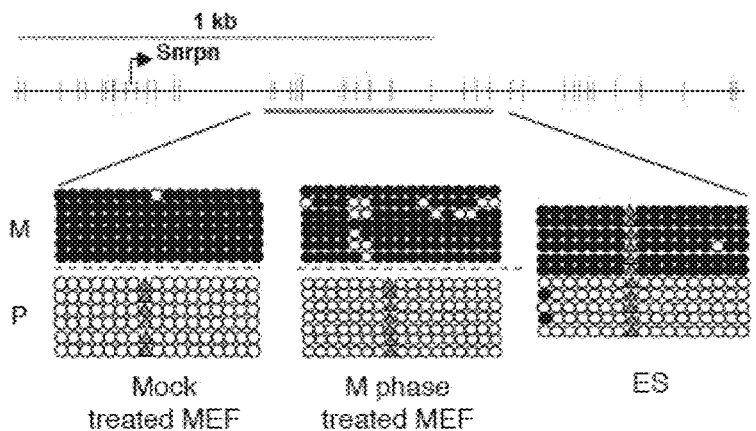

FIGS. 11A-C: the incubation with M phase *Xenopus* egg extracts does not demethylate DNA of MEF nuclei Bisulfite sequencing was performed in mock-treated and M-phase treated MEF nuclei and ES cells. Amplified regions are indicated by a solid blue bar. Each horizontal row of circles represents the CpG dinucleotides of an individual molecule. Solid circles depict methylated CpGs, open circles unmethylated CpGs. The parental allele origin (M: maternal; P: paternal) was determined in MEFs and iPS cells by using DNA polymorphisms between C57BL/6J and JF1 backgrounds. Blue triangles show individual CpGs that are absent due to polymorphisms.

FIG. 11A represents the analysis of the promoter region of Oct4.

FIG. 11B represents the analysis of the promoter region of Nanog.

FIG. 11C represents the analysis of the promoter/imprinting control region of the imprinted Snrpn gene.

Figure 12:
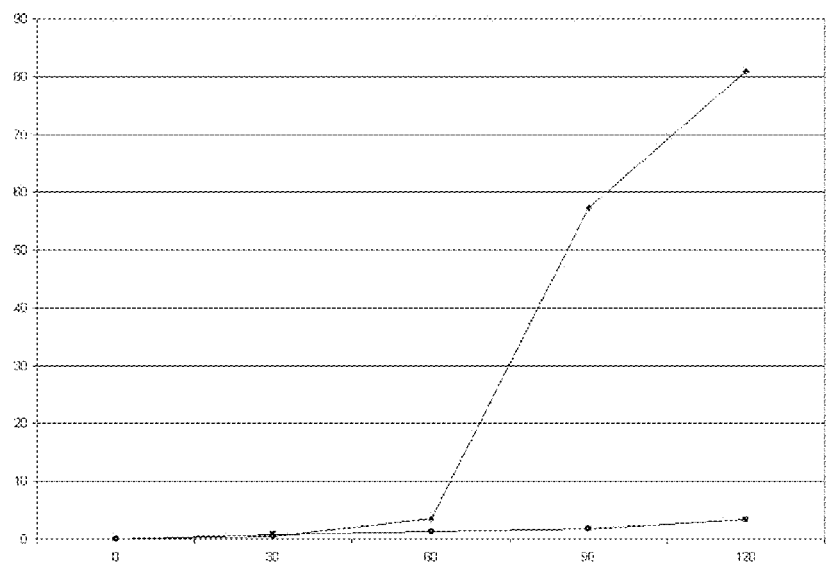

FIG. 12: Stability of the blockage of the isolated extract of female germinal cells in metaphase.

Y-axis represents the % of DNA synthesis, and X-axis represents the incubation time in min.

Capacity of the isolated extract blocked in phase M to synthesize DNA with Ca2+ (diamonds), or without Ca2+ (square), is measured by incorporation of $[^{32}P]\alpha dCTP$.

When the extract is blocked in metaphase, it does not synthesize DNA without Ca2+, but it synthesizes DNA in presence of Ca2+.

EXAMPLES

Example 1

Extract Preparation

Mitotic extracts are prepared through a procedure similar to that used for interphasic extract. Eggs should not be activated, however, and EGTA should be added to buffers to chelate traces of calcium, either present in solutions or released from intracellular stores.

1. Set the centrifuge at 1° C. Cool all tubes, adaptors, and syringes to 4° C. before starting the preparation of the extract.
2. Transfer the eggs to a glass beaker and rinse with HSB (HSB-CSF: 15 mM Hepes pH 7.6; 110 mM NaCl; 2 mM KCl; 1 mM MgSO4; 0.5 mM Na2HPO4; 2 mM NaHCO3+2 mM EGTA). It is advantageous to pool the eggs from the same frogs.
3. Add distilled water and leave the external jelly coat to swell for 5 min at room temperature.
4. Add HSB-CSF 0.3×, cysteine 2%, pH 7.9 (the solution should be used within 6 hrs of preparation), and dejelly by gentle swirling at intervals. This takes 5 to 10 min and complete removal of the jelly is obtained when the eggs can be tightly packed together, slightly deformed. It is important to obtain a complete dejellification. At this stage, success depends on both the rapidity with which the preparation is done and the strict observation of the cold temperature conditions after step 10.
5. Rinse immediately at least 5 times with 100-200 ml HSB-CSF per ml of eggs. If at this point necrosis is visible in more than 20% of the eggs, do not proceed further. Transfer to 50-ml glass beaker.
6. Transfer the eggs in a large glass Petri dish for observation under a microscope. Eggs should not show any signs of spontaneous activation.
7. Transfer to a cold Ultra-clear tube. Rinse with cold XB-CSF (10 mM HEPES pH 7.7; 100 mM KCl; 1 mM MgCl2; 5% Sucrose; 1 mM DTT; 5 mM EGTA) containing 10 μg/ml protease inhibitors and 100 μg/ml cytochalasin B. Use 1 ml for 3 ml eggs.
8. Leave the tube in ice for 5 to 10 min to chill the eggs.
13. Remove the excess buffer and pack the eggs by centrifugation at 150 g, 45 sec, 1° C., in a Sorvall swinging rotor or equivalent.
14. Rapidly remove the excess buffer and centrifuge at 17,000 g (Sorvall HB4 swinging rotor, 10K), for 10 min at 1° C. The centrifugation crushes the eggs and the soluble content is thus exuded.
15. Withdraw the extract by puncturing the side of the tube with a 20-gauge needle inserted into a 1 to 5 ml syringe, depending on the amount of soluble extract. Insert the needle just above the black pigment layer and collect the cytoplasmic layer, avoiding the yellow lipid top layer. Transfer to a cold Ultra-clear tube. Add 10 μg/ml protease inhibitors, 10 μg/ml cytochalasin B, 1/20 volume Energy Mix 20× (Energy Mix—CSF 20×: 200 μg/ml Creatine Kinase; 200 mM Creatine Phosphate; 20 mM ATP; 20 mM MgCl2; +2 mM EGTA), and 5% glycerol. Mix gently.
16. Centrifuge again in the same conditions.
17. Collect the supernatant in a cold tube. If necessary, add 200 μg/ml cycloheximide to prevent protein synthesis. Store at −80° C. in 100 or 200 μl aliquots previously frozen in liquid nitrogen. Protein concentration in low speed extracts is around 50 mg/ml and RNA concentration, mainly in ribosomes, is 5-10 mg/ml. Aliquots should be used only once and should not be frozen again after thawing.

Example 2

Synergic Induction of Pluripotent Cells by Combined Exposure to Mitotic Egg Extracts and Transcription Factors Introduction Nuclear transfer (NT) experiments in frogs and then in mammalian eggs have demonstrated that somatic cells can be reprogrammed to pluripotency (1-4). More recently, induction of pluripotency in somatic cells by ectopic expression of the four transcription factors Oct4, Klf4, Sox2 and c-Myc (OKSM) has been used to produce induced pluripotent stem (iPS) cells, which are highly similar to embryonic stem (ES) cells. Notably, murine iPS cells have a complete developmental potential as demonstrated by their capacity to form teratomas, generate chimeras and contribute to the germline. However, the efficiencies of both iPS cell production and NT remain low and most of the obtained reprogrammed cells appear to be only partially reprogrammed. The epigenetic memory of the cell is one key barrier, which has to be overcome to efficiently reprogram differentiated cells (5). Thus, additional factors may be needed to improve reprogramming efficiency (6, 7) and many efforts have been done over the last years to optimize these procedures. It has been suggested that different reprogramming strategies could be associated to synergize their efficiencies (8). Several attempts have been made by using cellular extracts to reprogram somatic cells, but they failed to reproduce the range of effects obtained by NT.

In NT experiments, reprogramming is induced by exposure of transplanted nuclei to the cytoplasm of the receiving oocyte. However, NT reprogramming appears hard to study in vitro due to the difficulty to obtain large quantities of mammalian oocytes. Xenopus eggs, which can be obtained in large amounts, can remodel the nuclear lamina of reversibly permeabilized mammalian cells (9) and Xenopus egg extracts can up-regulate Oct4 expression in cells that already express Oct4 (10), similarly to what observed when adult mouse nuclei are injected in Xenopus oocytes (11). More recently, it was reported that the replication origin pattern and chromosome organization of Xenopus erythrocyte nuclei could be remodeled by metaphase-arrested extracts (M phase extracts) from Xenopus eggs (12). The Inventors further investigated whether pre-incubation of mouse embryonic fibroblasts (MEFs) with Xenopus egg extracts could increase the efficiency of NT and iPS production. The Inventors show that M phase, but not interphase, Xenopus egg extracts increased NT efficiency and engaged MEFs into a stem cell program. They also induced a global change of MEF chromatin structure and replication properties. In particular, M phase extracts reset the level of several epigenetic marks in MEF nuclei, independently of their role in chromatin activation. Moreover, M phase extracts, but not interphase extracts, partially reprogrammed permeabilized MEFs to form colonies, which expressed pluripotency markers. Finally, iPS cell induction by ectopic expression of OSKM was 45-fold increased when MEFs were incubated in M phase Xenopus egg extracts. The resulting iPS cells were fully reprogrammed, as shown by their capacity to produce chimeras and colonize the germline.

Results

Figure 1A:
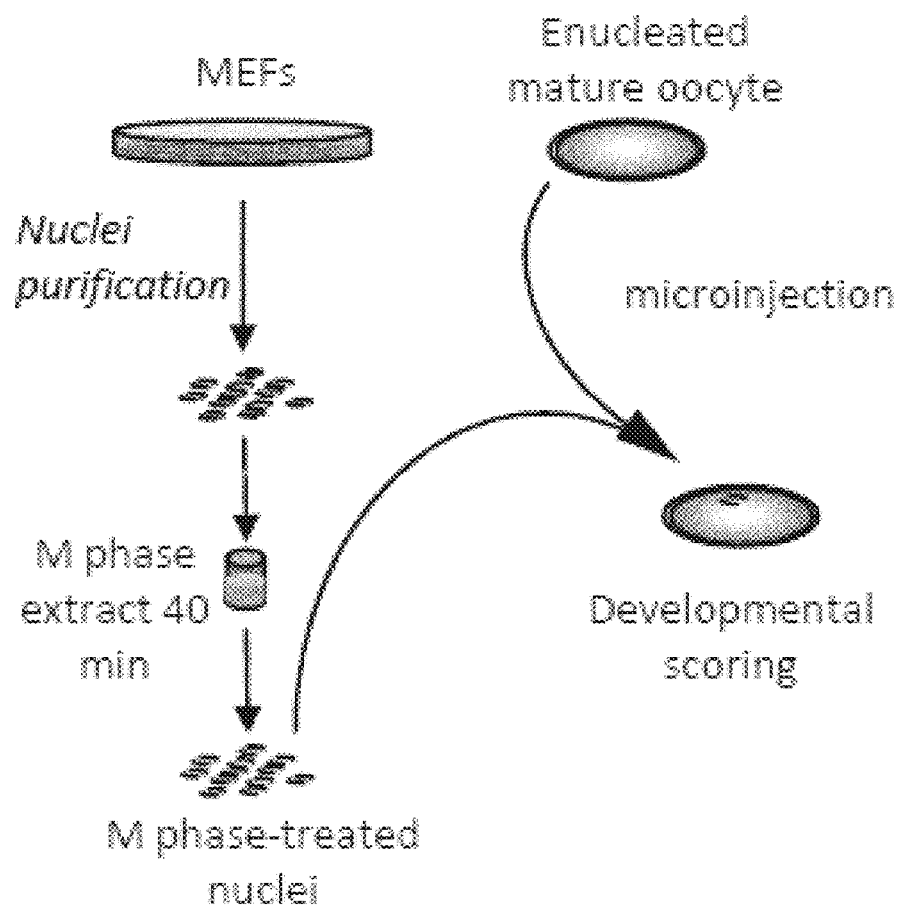
Figure 1B:
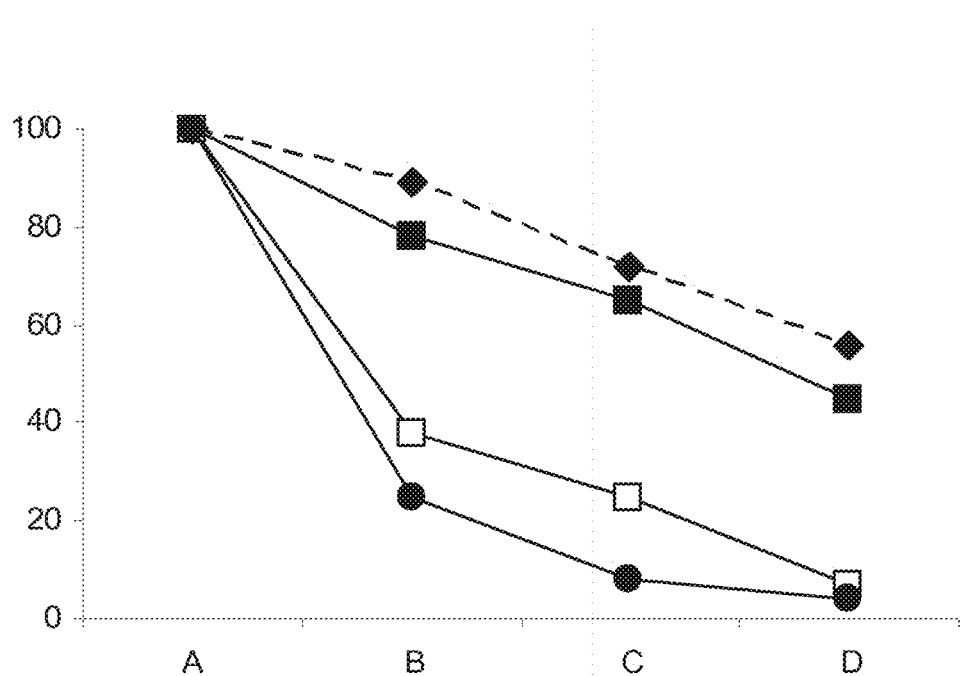

Pre-Treatment with M Phase Xenopus Egg Extracts Improves Efficiency of Both Nuclear Transfer and iPS Cell Production in Mammals The Inventors first asked whether M phase Xenopus egg extracts could improve the highly inefficient NT of MEFs (13). Permeabilized MEF nuclei in G1 phase were pre-incubated with M phase (FIG. 1A) or interphasic Xenopus egg extracts or buffer alone and their progression to blastocyst stage, after NT, was compared. NT of G1 MEFs nuclei led to 11% blastocysts (FIG. 1B and Table 1), a value that was significantly lower than what obtained after NT of metaphase ES nuclei (55%), which were previously described as the best donor nuclei for NT (14). Conditioning MEF nuclei in M phase egg extracts significantly increased the rate of blastocyst formation to a level comparable to that obtained with metaphase ES nuclei (45%) (FIG. 1B and Table 1). These data show that M phase *Xenopus* egg extracts efficiently improve reprogramming of somatic cells by NT. Conversely, pre-incubation with interphasic egg extracts did not improve but rather slightly decreased NT efficiency (3%), indicating the importance of the mitotic state of the reprogramming extract. Since both mitotic MEFs and G1 ES nuclei were relatively inefficient donors for NT in metaphase-blocked oocytes (summarized in Table 1), in Inventor's results also suggest that treatment with M phase *Xenopus* extracts can remodel MEF nuclei toward both a mitotic and pluripotent state.

Figure 1C:
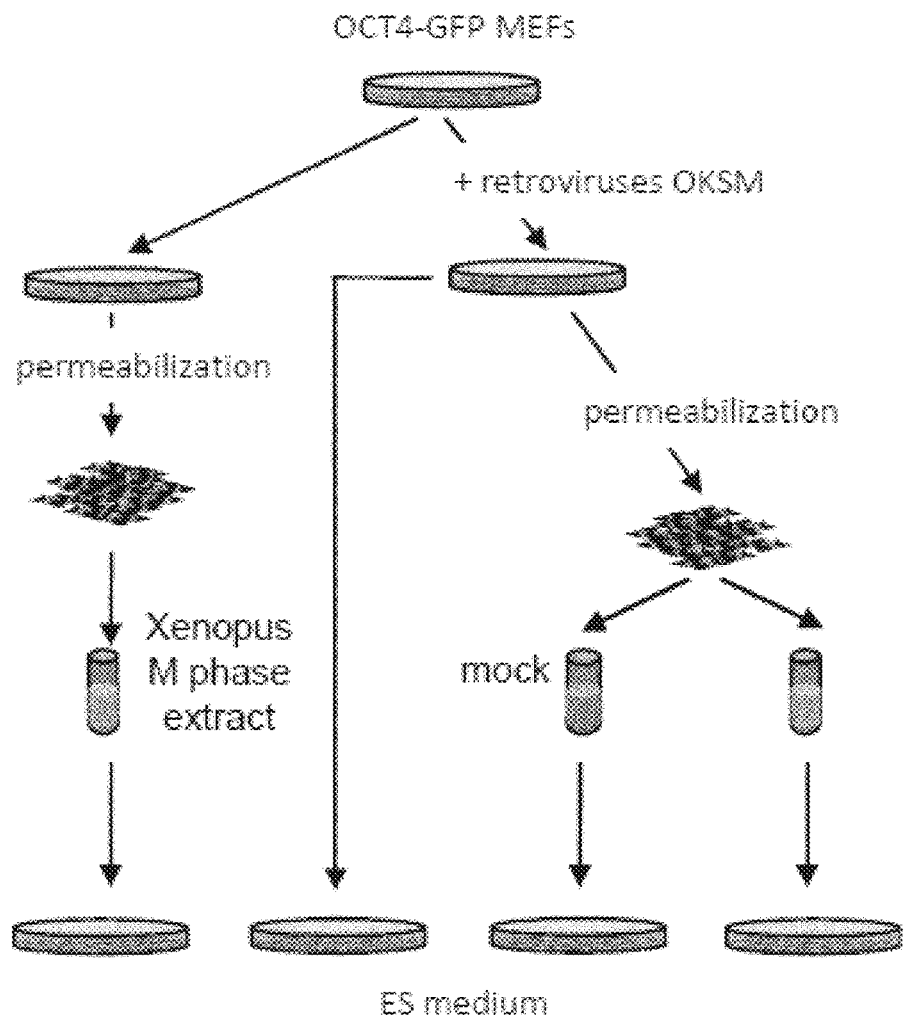
Figure 1D:
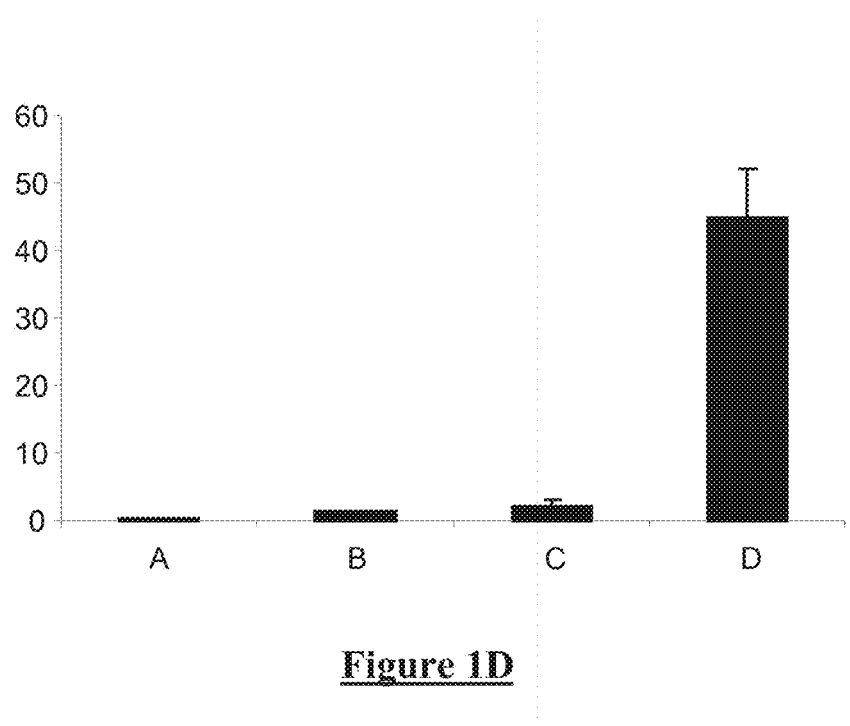

The Inventors then checked whether treatment with M phase *Xenopus* egg extracts could also improve the efficiency of iPS cell production. The generation of iPS cells by viral-mediated expression of the OSKM transcription factors in mouse and human cells, although with low efficiency, was a breakthrough in reprogramming of somatic cells to a pluripotency state (15-19). The Inventors therefore combined OSKM over-expression and incubation with M phase *Xenopus* egg extracts (M-iPS cells) using the experimental strategy shown in FIG. 1C. OCT4-GFP MEFs were infected with retroviruses encoding the four transcription factors, permeabilized, incubated with M phase extracts and then resealed onto gelatine-coated plates in ES medium. The Inventors checked by quantitative PCR that the M phase extract treatment did not influence the viral integration of the OKSM transgenes (FIG. 7). Seven days after infection, the Inventors determined the proportion of OCT4-GFP positive colonies, which is related to full reprogramming events since endogenous OCT4 re-expression has been reported to be a stringent reporter of reprogramming (2). The number of GFP positive colonies was 45-fold higher in OSKM-induced cells exposed to M phase egg extracts (M-iPS cells) than in cells that over-expressed only OSKM, with or without treatment with streptolysin-O (SLO) (FIG. 1D). Thus, a short incubation of mammalian somatic cells in M phase *Xenopus* egg extracts greatly increases the yield of fully reprogrammed iPS cells.

Characterization of M-iPS Cells

M-iPS cells presented an ES-like morphology and uniform expression of the pluripotency markers alkaline phosphatase, OCT4, NANOG, and SSEA1 (FIGS. 2A-S). Moreover, the levels of expression of different pluripotency markers were measured by quantitative PCR and were similar to those in ES cells (FIGS. 2T-U). The transcriptomic profile of M-iPS cells, MEFs and ES cells were analyzed (FIG. 7) and scatter plots of DNA microarrays analyses confirmed the similarity between M-iPS and ES cells ($R^2=0.9175$). Efficient reprogramming has been tightly linked to hypo-methylation of DNA on promoters of key regulators of pluripotency, such as Oct4 and Nanog [Maherali N, et al. *Cell Stem Cell*. 2007 Jun. 7; 1(1): 55-70]. The DNA methylation profiles of M-iPS cells and ES cells were similar (FIGS. 8A-B), confirming the efficiency of reprogramming obtained by combining M phase *Xenopus* egg extracts and OKSM expression.

The Inventors then investigated the ability of M-iPS clones to differentiate. When induced to differentiate, all tested M-iPS clones formed embryoid bodies (FIG. 3A-F) and the stem cell markers Oct4, Nanog and Klf4 were down-regulated (FIG. 10), whereas markers of differentiation in the three germ layers were up-regulated with levels comparable to those observed in embryoid bodies obtained from ES cells (FIG. 10) and (20-23).

Finally, the complete reprogramming of the M-iPS clones was demonstrated in vivo by the capacity of two different clones, one male and one female, to produce adult chimeras after injection into CD1 blastocysts (FIGS. 3G-I and Table 2). In addition, germline transmission was also successful as shown by the production of F1 black offspring (due to the B6×JF1 genetic background) after mating these chimeras with CD1 albino animals (FIG. 3J).

The Inventors conclude that M phase *Xenopus* egg extracts have a strong positive effect on the efficiency of iPS cell production. Importantly, this action is not additional but synergistic, since the reprogramming efficiency (number of GFP-positive colonies, see FIG. 1D) when the two strategies are combined is much higher than the simple addition of their respective efficiency.

TABLE 1 represents the in vitro development of embryos obtained using MEF nuclei exposed to M phase *Xenopus* egg extracts and injected into enucleated mouse oocytes

| | recon-structed | activated | 2-cell | % of 2-cell embryos | | |
|---|---|---|---|---|---|---|
| | | | | 4/8-cell | morula | blastocyst |
| Mitotic ES cells | | 175 | 154 | 87% (134) | ND | 55% (84) |
| G ES cells* (Zhou et al. 2001 | 39 | 36 | 28 | ND | 28% (8) | 11% (3) |
| G1 MEFs | 263 | 195 | 140 | 56% (79) | 27% (38) | 11% (16) |
| Mitotic MEFs** (Li et al. 2003) | ND | ND | ND | ND | ND | 6% |
| MEFs + interphasic extracts | 178 | 84 | 30 | 27% (8) | 7% (2) | 3% (1) |
| MEFs + M phase extracts | 148 | 87 | 49 | 78% (38) | 67% (33) | 45% (22) |

Percentage of embryos relative to 2-cell embryos obtained after nuclear transfer of ES nuclei and MEF nuclei that had been pre-incubated in mock buffer, interphase or M phase *Xenopus* egg extracts. Mitotic and G1 ES nuclei were isolated and injected as previously described (33) and mitotic MEF nuclei as in Li et al. (13).
*refers to sv129/sv cell line;
**refers to 129/Svpas cell line.

TABLE 2 represents the developmental potential of iPS cells derived from MEFs exposed to M phase *Xenopus* egg extracts (M phase iPS cells).

| | Injected blasto-cysts | Born embryos | Number of chimeras | % of chimeras | Female chimeras | Male chimeras |
|---|---|---|---|---|---|---|
| Clone #1 (male) | 233 | 71 | 31 | 46% | 25 | 6 |
| Clone #2 (female) | 85 | 10 | 7 | 70% | 3 | 4 |

Percentage of chimeras obtained after injection of two different clones of M phase iPS cells (one male and one female) into CD1 blastocysts and analysis of their ability to colonize the germline.

*Xenopus* M Phase Egg Extracts Partially Reprogram Mammalian Fibroblasts

To characterize the synergistic effect of M phase *Xenopus* egg extracts, the Inventors first asked whether this treatment alone could modify the limited proliferation potential of MEFs (24). Treatment with M phase egg extracts strongly increased the proliferation rate of MEFs during at least two cell cycles (FIG. 4A) and induced also the formation of a few colonies that expanded over a few days before growth arrest (FIG. 4B-G). These colonies were less numerous than upon M-iPS cell induction and were never seen in mock-treated MEFs.

Growth stimulation was also accompanied by expression of pluripotency cell markers, which were never observed in mock-treated cells. Indeed, alkaline phosphatase expression (a marker of partial reprogramming) was induced upon M phase treatment (FIGS. 4K-M) and endogenous expression of OCT4, a more stringent marker of pluripotency (2), was detected in colonies by immuno fluorescence as well as GFP expression driven by the Oct4 promoter (FIGS. 4H-J). Interestingly, alkaline phosphatase was expressed in a relatively high proportion of M phase extract-treated cells, including those that did not progress further to form colonies (FIGS. 4K-M). The presence in several independent experiments of clones that expressed OCT4, or alkaline phosphatase, or both suggests that M phase egg extracts favor the development of a heterogeneous cell population with different levels of reprogramming. This is in agreement with the heterogeneity observed during the production of iPS cells by using OSKM over-expression and it is likely to be the result of a stochastic process (25). These results indicate that M phase extracts alone can change the cell cycle properties and can induce a partial and transient reprogramming of MEFs.

Seven days after treatment with M phase egg extracts, the expression of the pluripotency markers Oct4, Nanog and Rex1 was confirmed by quantitative RT PCR (FIG. 4E) in whole unselected cell populations, as pluripotency markers were often detected before colony formation. Primers used for Q-PCR analyses were specific for mouse transcripts and they could not amplify RNA from M phase *Xenopus* extracts, confirming the induction of expression of the endogenous mouse genes. In addition, Zfpm2, a transcription factor expressed in MEFs but not in ES cells (18), was down-regulated after exposure to M phase egg extracts (FIG. 4N).

Overall, the Inventors' data suggest that M phase *Xenopus* egg extracts alone are sufficient to partly reprogram MEFs, as indicated by the up-regulation of pluripotency genes and down-regulation of genes normally expressed in MEFs and the rapid but transient induction of proliferation. Neither of these effects was observed when using interphase *Xenopus* egg extracts, in agreement with the previously reported failure to reprogram cells using *Xenopus* egg extracts described in (26).

Treatment with M-Phase *Xenopus* Egg Extracts Induces Mitotic Features and Modifies the Global Epigenetic Signature The observations that only M phase and not interphasic *Xenopus* egg extracts had a reprogramming effect on reversely permeabilized MEFs as well as on NT efficiency indicate that the mitotic stage of the donor extract is crucial. Therefore, the inventors investigated whether exposure of MEFs at the G1 phase to M phase egg extracts could induce mitotic markers in the reprogrammed nuclei. Indeed, exposure to M phase *Xenopus* egg extracts drove MEF nuclei into a mitotic-like stage, accompanied by modification of the chromatin structure (FIGS. 5A-D) followed by global condensation, as shown by the formation of condensed chromatin fibers (FIGS. 5E-G). MEF nuclei exposed to M phase egg extracts also showed phosphorylation of histone H3 on Ser 10, and dissociation of the nuclear envelope component Lamin B1 (27, 28), a factor involved in the nuclear structure (FIGS. 5H-O and 5R), all distinctive features of entry in mitotic phase.

Exposure to M phase egg extracts also appeared to erase the chromatin superstructure organization, as revealed by the loss of heterochromatin foci visualized by DAPI staining together with the loss of HP1 expression (FIGS. 5A-R). The Inventors thus further investigated whether M phase egg extracts modified the global epigenetic signature of MEF nuclei. The Inventors first determined the level of histone acetylation because it has been shown that the histones of the donor nuclei are deacetylated during NT (29, 30). Western blots analysis showed that incubation of MEF nuclei with M phase *Xenopus* egg extracts reduced the level of acetylation of H3 (particularly H3K9) and of H4 at Lysine 8 (FIGS. 5S-AB).

The Inventors then asked whether the *Xenopus* egg extracts could also modify the histone methylation profiles, as histone hypomethylation has been correlated with the epigenetic plasticity of somatic mammalian cells (31). A short incubation of MEF nuclei with M phase *Xenopus* egg extracts globally reduced the level of H3K9me2-me3, H4K20me3 and H3K4me2-me3 as shown by western blotting (FIGS. 5S-AB). Conversely, the level of H3K27me3 did not change upon incubation with M phase extracts, suggesting that this mark is more stable. The global demethylation at H3K9 might contribute to the improvement of NT efficiency following incubation with M phase egg extracts because maintenance of H3K9 tri-methylation has been associated with developmental failure during NT (32). Altogether, these results show that incubation with M phase *Xenopus* egg extracts broadly modifies the epigenetic signature of mammalian somatic nuclei by resetting several, but not all, epigenetic marks.

Moreover, incubation with M phase *Xenopus* egg extracts also induced a reduction of the global level of the histone variant H3.3, which has been recently implicated in cell identity memory during reprogramming by NT (33) (FIGS. 5S-AB).

Finally, the Inventors analyzed the DNA methylation profile, another key marker of cell memory. Bisulfite sequencing was performed and showed that incubation in M phase *Xenopus* egg extracts for 40 minutes did not modify the DNA methylation status of the pluripotency genes Oct4 and Nanog (FIGS. 11A-C).

In summary, *Xenopus* M phase extracts drive MEF nuclei into a mitotic state and also remodel their chromatin structure. These results could explain the strong synergistic effect of the treatment with M phase *Xenopus* extract on NT and iPS cells production.

MEF Nuclei are Adapted to an Embryonic Replication Program when Pre-Incubated in M Phase *Xenopus* Egg Extracts.

The Inventors previously showed that M phase *Xenopus* egg extracts could reset the replication program of nuclei from differentiated *Xenopus* cells and allow the transition from a somatic to an embryonic profile of DNA replication (12). The Inventors thus asked whether MEF nuclei could be similarly reprogrammed. To this aim nuclei from MEFs synchronized in G1 were incubated either with interphasic *Xenopus* egg extracts or first exposed to M-phase egg extracts before transfer into interphasic egg extracts and then their ability to replicate DNA was assessed (FIG. 6A). Nuclei exposed only to interphase egg extracts did not (or very poorly) replicate DNA (FIG. 6B). Conversely, pre-incubation of MEF nuclei in M phase egg extracts induced DNA replication with a kinetic nearly similar to that of *Xenopus* sperm nuclei when further transferred to an interphase extract (FIG. 6C). The Inventors conclude that mouse somatic nuclei passing through mitosis in *Xenopus* egg extracts are partially reprogrammed and acquire the accelerated rate of DNA replication characteristic of *Xenopus* early embryos.

Discussion

Reprogramming of Mouse Embryonic Fibroblasts by *Xenopus* Egg Extracts

The experiments described here show that a short incubation of mammalian somatic nuclei or cells with M phase *Xenopus* egg extracts improves the efficiency of both NT and iPS cell production. This suggests the existence of common barriers limiting the efficiency of reprogramming by NT and iPS cells that pre-incubation in M phase *Xenopus* egg extract might help removing these barriers. Moreover, the results presented here also emphasize that combining different strategies can improve the reprogramming of mammalian somatic cell nuclei. Neither NT nor heterocaryons can be used in combination with iPS cells due to technical limitations. However, *Xenopus* egg extracts can be obtained in large amount and can be used to increase the yields of iPS cells.

The Inventors show that incubation with M phase *Xenopus* egg extracts is sufficient to improve the efficiency of NT using MEF nuclei up to the level observed with pluripotent ES cells. Furthermore, reversibly permeabilized MEFs incubated in M phase *Xenopus* egg extracts acquire several features of pluripotent cells, such as induction of cell proliferation, formation of colonies, expression of ES cell markers, including the expression of OCT4, one of the most stringent marker of pluripotency (34). This reprogramming activity is not stable; colonies stop growing after a couple of rapid cell cycles. However, this partial reprogramming activity is enough to increase by 45-fold the production of fully reprogrammed iPS cells by viral transduction of OKSM. This synergic effect is probably underestimated since the proportion of efficiently permeabilized MEFs does not exceed 30% in the Inventors' hands. The resulting M-iPS clones appear to be well reprogrammed since the obtained clones could efficiently produce chimeras and colonize the germline. This synergic effect suggest that incubation in *Xenopus* egg extracts can induce modifications of the genome features of somatic mammalian cells, thus opening a larger window of action for reprogramming by NT or OKSM expression.

Importance of Exposure to Mitotic/Meiotic Conditions for Reconditioning Differentiated Nuclei The Inventors' experiments show that the mitotic state of the *Xenopus* egg extracts is crucial. *Xenopus* interphasic egg extracts neither induced reprogramming in permeabilized MEFs nor improved NT efficiency. Conversely, M phase *Xenopus* egg extracts induced a global mitotic signature in G1 MEF nuclei, as revealed by the phosphorylation of histone H3 on Ser 10 and remodeling of the nuclear structure. This global reorganization of chromatin at mitosis is likely to be critical for the reprogramming activity of M phase *Xenopus* egg extracts. Transition through mitosis has always been found to be crucial in NT experiments performed in the mouse, where zygotes temporally arrested in mitosis support nuclear reprogramming much more efficiently that interphase zygotes (35). Altogether, these results indicate that efficient reprogramming requires not only an early embryonic pluripotent context, but also transition through mitosis.

Incubation of donor somatic nuclei in mitotic egg extracts could help resynchronizing the cell cycle of donor nuclei to make them compatible with an early development context. The Inventors show that MEF nuclei, like *Xenopus* somatic cell nuclei but differently from sperm nuclei, are not competent to replicate their genome in interphasic *Xenopus* egg extracts. The requirement of a mitotic reprogramming phase may explain why, in NT experiments, nuclei from half-cleaved embryos develop much better than nuclei from normal blastulae (36). Indeed, such nuclei were derived from embryos that failed to divide during the $1^{st}$ cleavage, implying that they should have gone through a mitotic stage before entering in S phase. In mouse, inefficient development occurs when nuclei are transferred into pre-activated oocytes, whereas the best developmental rates are observed when activation occurs 1-3 hours after nuclei transfer (37). The Inventors' observations provide an explanation to these data by showing that mitotic, but not interphasic *Xenopus* egg extracts can reprogram differentiated cells.

M Phase *Xenopus* Egg Extracts Remodel the Global Organization of Somatic Mammalian Genomes In addition to the cell cycle synchronization effects, conditioning nuclei in a mitotic embryonic context may facilitate reprogramming of gene expression. During mitosis, most pre-existing transcription and replication factors are erased from chromatin (38). For instance, TBP, the main component of the transcription machinery which is required for transcription by all three polymerases, as well as TFIIB are removed from the chromatin of somatic cell nuclei incubated in egg extracts, together with the disappearance of the nucleoli (39). The Inventors' experiments show that M phase *Xenopus* egg extracts efficiently induce a global mitotic signature in G1 MEF nuclei, as revealed by the loss of HP1, phosphorylation of histone H3 on Ser 10 and remodeling of the nuclear structure. Interestingly, marks associated with transcriptional repression (H3K9me2, H3K9me3, H4K20me3) and with active chromatin (acetyl H4K8, acetyl H3K9, H3K4me3, H3K4me2) are both reduced in chromatin of MEF nuclei incubated with M phase extracts. This event is reminiscent of the atypical bivalent epigenetic signature of ES cells (40) and could promote reprogramming by resetting the memory of the somatic nuclei. Histone demethylation also appears to be an interesting feature of the action of the M phase *Xenopus* egg extracts. However, the reduction of epigenetic marks is not complete, suggesting that some defined nuclear structures could remain after incubation with M phase extracts.

The Inventors' results show that pre-incubation with M phase *Xenopus* egg extracts can recapitulate reprogramming events occurring during NT. Indeed, they explain the global epigenetic modifications that have been described during reprogramming of mammalian somatic nuclei injected in non-activated, metaphase II mammalian oocytes (29, 30, 41). Thus, *Xenopus* egg extracts could provide a powerful tool to biochemically study molecular events occurring during NT.

The global reorganization of chromatin at mitosis is likely to be crucial for the reprogramming activity by M phase *Xenopus* egg extracts. These extracts have the advantage of providing all the genetic and epigenetic factors involved in mitosis as well as in pluripotency, as opposed to reprogramming through ectopic expression of a few genes. The combination of both methods leads to a strong synergistic effect, demonstrating the evolutionary conservation of reprogramming circuits.

Material and Methods

Cells and Media

MEFs were derived from 13.5E wild type mouse embryos or from C57BL/6J-JF1 embryos hemizygous for the OCT4-GFP transgenic allele. Gonads, internal organs and heads were removed before MEF isolation. MEFs were then expanded in high-glucose DMEM (Invitrogen) supplemented with 10% ES-tested fetal bovine serum (cat N° S1810, Biowest), 2 mM L-glutamine (Invitrogen), 1 mM sodium pyruvate (Sigma). MEFs were used up to passage 5. OCT4-GFP mice were initially created by Pr. Schöler (42) and obtained from Pr. Surani (Wellcome Trust/Cancer Research UK Gurdon Institute, Cambridge). The ES cell line CGR8 was obtained from Dr C. Crozet (Institut de Génétique Humaine, Montpellier). ES cells were grown on 0.1% gelatin without feeders. They were cultured at 37° C. in 5% $CO_2$ in ES medium: GMEM supplemented with 10% fetal calf serum, 0.1 mM β-mercaptoethanol, 1 mM sodium pyruvate, 1% non-essential amino acids (Gibco), 2 mM L-glutamine, in the presence of 1000 U/ml LIF (ES-GRO).

*Xenopus* Egg Extract Preparation and Replication Reactions

*Xenopus* mitotic and interphasic egg extracts as well as demembranated sperm nuclei were prepared and used as described in Lemaitre et al. (12), Menut et al. (43) and the detailed protocol available at www.igh.cnrs.fr/equip/mechali/. MEF nuclei were prepared from confluent MEFs at early passages (up to P5) following the procedure described for *Xenopus* erythrocyte nuclei (12). Briefly, MEFs were trypsinized and washed twice with PBS. MEFs were incubated in hypotonic buffer (10 mM KHEPES pH7.5; 2 mM KCl; 1 mM DTT; 2 mM $MgCl_2$; 1 mM PMSF; protease inhibitors) for 1 hour. Swelled cells were then homogenized with 20 to 30 strokes and then incubated in hypotonic buffer containing 0.2% Triton X-100 on ice for 3 minutes. Nuclei were washed twice in isotonic buffer (10 mM KHEPES, 25 mM KCl, 2 mM $MgCl_2$, 75 mM sucrose and protease inhibitors). Nuclei were finally centrifuged through a 0.7M sucrose cushion and resuspended in isotonic buffer supplemented with 20% sucrose. Sperm nuclei and MEF nuclei (1000 nuclei/µl and 500 nuclei/µl respectively) were incubated in S phase or M phase (CSF) extracts. DNA synthesis was measured by [$^{32}P$]αdCTP incorporation in *Xenopus* interphasic egg extracts as previously described (43). Nuclei transfer from M phase extracts to interphasic extracts was performed as described previously (12).

Streptolysin-O Permeabilization and M Phase Extract Treatment

MEFs were permeabilized with streptolysin-O (SLO) mainly as described by Taranger et al. (44). Briefly, MEFs were trypsinized, washed twice in PBS and then resuspended in cold $Ca^{2+}$ and $Mg^{2+}$-free Hanks' Balanced Salt Solution (HBSS) at 1000 cells/µl with 250 ng/µl SLO (Sigma S0149). Cells were incubated at 37° C. with gentle agitation for 50 min and then washed twice with ice cold HBSS. Permeabilized cells were incubated in M phase *Xenopus* egg extracts or buffer (1000 cells/µl of extracts) for 40 min, washed twice in HBSS and resealed on gelatin in complete ES medium supplemented with 2 mM $CaCl_2$ for 2 hours and then cultured in complete ES medium.

M Phase-Extract Treated iPS Cells Production

Constructs in pMXs retroviral vectors encoding Oct4, Sox2, Klf4 and c-Myc (obtained from Addgene) were transfected in Platinum HEK cells using the Lipofectamine 2000 transfection reagent (Invitrogen), according to the manufacturer's recommendations. 30 µl of Lipofectamine 2000 were added to 750 µl OPTIMEM and mixed with 12 µg DNA that had been diluted into 750 µl OPTIMEM and incubated for 5 min. After 20 min incubation at 20° C., the DNA/Lipofectamine 2000 mixture was added drop by drop to Platinum HEK cells. 48 h after transfection, supernatants were collected, filtered through 0.45 µm Millex-HV (Millipore) filters and supplemented with 12 µg/ml polybrene. OCT4-GFP MEFs were seeded on 0.1% gelatin at a density of $8.10^5$ cells in 56 $cm^2$ Petri dishes and the four virus containing supernatants were pooled in equal amounts and added to the MEFs. 18 hours later, supernatants were removed and cells cultured in complete ES medium. Five-six hours later, cells were trypsinized and permeabilized with SLO as described above and then incubated either in mock buffer (HBSS) or in *Xenopus* M phase egg extracts for 40 min. After treatment, cells were washed twice and plated ($8.10^5$ cells per 56 $cm^2$) in gelatin-covered dishes with ES medium supplemented with 2 mM $CaCl_2$. After 2 hours, medium was removed and replaced by complete ES medium until appearance of OCT4-GFP positive colonies. M phase extract-treated OCT4-GFP positive colonies were mechanically isolated, individual cells dissociated and plated onto feeders for analysis that was performed after at least 15 passages on feeders.

Nuclear Transfer

Nuclear transfer experiments were performed mainly as described in Zhou et al. (45). Briefly, permeabilized MEF nuclei from confluent (B6×129) MEFs were freshly prepared as described above and either directly injected into enucleated, metaphase II mouse oocytes or pre-incubated in M phase or interphasic *Xenopus* egg extracts for 40 min. Before injection, pre-incubated nuclei were washed twice in M16 medium to eliminate the *Xenopus* egg extract. Before injection, the efficiency of treatment and chromatin integrity were assessed by visually inspecting the nuclei with a phase contrast microscope. (B6×129) metaphase ES cells were isolated as described in Zhou et al. (45).

Differentiation of ES Cells or M Phase Extract-Treated iPS Cells.

ES cells or M phase extract-treated iPS cells were dissociated into single cell suspensions with 0.05% trypsin/EDTA and plated at low density in non-adherent bacterial Petri dishes with standard ES culture medium (without LIF). After 2 days, medium was replaced with ES culture medium supplemented with 0.5 µM retinoic acid to induce differentiation of embryoid bodies.

Reprogramming Efficiency

Reprogramming efficiency after M-phase extracts treatment was analyzed seven days after infection. The number of OCT4-GFP positive colonies induced by the different treatments was counted under a fluorescent microscope and compared with the number of colonies obtained from non-permeabilized OKSM-infected MEFs from the same infection experiment. Alkaline phosphatase staining was performed using the Alkaline Phosphatase Detection Kit from Sigma Diagnostics according to the manufacturer's procedure. For immunofluorescence, cells in culture were washed once in PBS and then fixed in 3% paraformaldehyde at room temperature (RT) for 15 minutes, washed with PBS and permeabilized with PBS/0.2% Triton X-100 for 5 min. Cells were then washed three times in PBS with 2% BSA for 10 minutes, incubated with anti-OCT-3/-4 (C-10) (Santa-Cruz, sc-5279), anti-NANOG (Abcam, ab21603) or anti-SSEA1 (clone 16MC480) (Abcam, ab16285) antibodies for 1 hr and then with the secondary antibody for 1 h after 3 washes in PBS. DNA was stained with DAPI. Immunofluorescence analysis of M phase extract- or mock-treated MEF nuclei was performed by spinning the treated nuclei onto coverslips by centrifugation at 100 g after having been 10-fold diluted in XB buffer (XB: 100 mM KCl, 0.1 mM $CaCl_2$, 1 mM $MgCl_2$, 10 mM KOH-HEPES [pH 7.7], 50 mM sucrose supplemented with protease inhibitors) as described previously (43).

Quantitative Reverse Transcriptase (RT)-PCR Analysis

For transcriptional analysis, total RNA was isolated from whole cell populations using the RNAeasy Mini Kit and RT was performed using the High Capacity cDNA Reverse Transcription Kit (Applied Biosystems). Quantitative PCR was performed on a Lightcycler 480 apparatus using the Lightcycler 480 SYBR Green I Master kit from Roche. Quantification data were normalized to the average expression of the endogenous Hprt1/Gapdh and β-Actin genes within the log-linear phase of the amplification curve obtained for each primer set using the ΔΔCt method. All samples were prepared in 2 to 3 biological repeats.

```
Primers for Quantitative RT-PCR:
Oct4
                                            (SEQ ID NO: 1)
Fw: ttctggcgccggttacagaaccatactcga (SEQ ID NO: 2)
Rev: gaggaagccgacaacaatgagaaccttcag Rex 1
                                            (SEQ ID NO: 3)
Fw: cagctcctgcacacagaaga (SEQ ID NO: 4)
Rev: actgatccgcaaacacctg Nanog
                                            (SEQ ID NO: 5)
Fw: ttcttgcttacaagggtctgc (SEQ ID NO: 6)
Rev: agaggaagggcgaggaga Zfpm2
                                            (SEQ ID NO: 7)
Fw: gcgaagacgtggagttcttt (SEQ ID NO: 8)
Rev: ggctgtcccatctgattc β-Actin
                                            (SEQ ID NO: 9)
Fw: gccggcttacactgcgcttctt (SEQ ID NO: 10)
Rev: ttctggcccatgcccaccat Gapdh
                                            (SEQ ID NO: 11)
Fw: tggcaaagtggagattgttgc (SEQ ID NO: 12)
Rev: aagatggtgatgggcttcccg Hprt1
                                            (SEQ ID NO: 13)
Fw: tcctcctcagaccgctttt (SEQ ID NO: 14)
Rev: cctggttcatcgctaatc Sox1
                                            (SEQ ID NO: 15)
Fw: gtgacatctgcccccatc (SEQ ID NO: 16)
Rev: gaggccagtctggtgtcag Sox17
                                            (SEQ ID NO: 17)
Fw: ctttatggtgtgggccaaag (SEQ ID NO: 18)
Rev: ggtcaacgccttccaagact Sox7
                                            (SEQ ID NO: 19)
Fw: gcggagctcagcaagatg (SEQ ID NO: 20)
Rev: gggtctcttctgggacagtg Brachyury
                                            (SEQ ID NO: 21)
Fw: cagcccacctactggctcta (SEQ ID NO: 22)
Rev: gagcctggggtgatggta Klf4
                                            (SEQ ID NO: 23)
Fw: gagttcctcacgccaacg (SEQ ID NO: 24)
Rev: cgggaagggagaagacact
```

DNA Microarrays Analysis

Total double strand cDNAs from ES cells, MEFs and M-iPS cells was hybridized on Nimblegen mouse expression 135K arrays and results were analyzed with the free trial Arraystar software. Normalization was calculated with the RMA algorithm (46) implemented in Bioconductor. The experiments were performed in triplicates.

Gene-by-gene tests for differential expression between paired cell types were performed using a moderated t-statistic (47). P-values were adjusted using the procedure of Benjamini and Hochberg for controlling the False Discovery Rate (FDR) (48). Differentially expressed genes between the paired cell types were identified using adjusted p values below 1%.

Bisulfite Sequencing

DNA extraction and bisulfite sequencing of mock-treated and M-phase treated MEF nuclei, M-iPS cells and CGR8 ES cells were performed as previously described (49). Before DNA extraction, GFP positive M-iPS cells were sorted with a Facsaria cytometer to avoid contamination by feeder cells. DNA polymorphisms between the C57BL/6J and JF1 backgrounds were used for allele discrimination in MEF and M-iPS cells.

```
Primers:
Bis-Oct4:
                                            (SEQ ID NO: 25)
Fw: TTAGAGGATGGTTGAGTGGGTTTGTAAGGAT (SEQ ID NO: 26)
Rev: CCA ATCCCACCC TCTAACCTTAACCTCTAA
(these primers amplify only the endogenous
copy of Oct-4.)

Bis-Nanog
                                            (SEQ ID NO: 27)
Fw: TAAATTGGGTATGGTGGTAGATAAGTTTGG (SEQ ID NO: 28)
Rev: TAAAAAACATCCTCTAATCTAAAAACATCC Bis-Snrpn
                                            (SEQ ID NO: 29)
Fw: ATTGGTGAGTTAATTTTTTGGA (SEQ ID NO: 30)
Rev: ACAAAACTCCTACATCCTAAAA
```

Generation of Chimeras

Chimeras were produced by injecting (B6-JF1) M-iPS cells into CD1 blastocysts that were subsequently implanted into pseudo-pregnant CD1 females. M phase extract-treated iPS clones were sexed by karyotyping.

Purification and Analysis of Chromatin Fractions

Permeabilized MEF nuclei were incubated in M phase *Xenopus* egg extracts for 40 min, diluted in 5 volumes of XB buffer and pelleted by centrifugation at 500 g through a 0.7M sucrose cushion for 10 min. Nuclear pellets were resuspended in XB with 0.2% Triton X-100 and incubated on ice for 5 min. Chromatin pellets were recovered by centrifugation at 5000 g for 5 min, adjusted in Laemmli buffer and analyzed by SDS-PAGE. Western blot analysis was performed using the following antibodies: anti-ser10 phosphorylated histone H3 (Ozyme, 9701S), anti-histone H3 (Abcam, ab1791), anti-HP1α (Millipore, MAB3584 or 2616), anti-histone variant H3.3 (Abcam, ab62642), anti-Lamin B1 (Abcam, ab16048), anti-H3K4me2 (Abcam, Ab7766), anti-H3K4me3 (Abcam, Ab1012), anti-H3K9me2 (Millipore, 07-441), anti-H3K9me3 (Upstate), anti-H4K20me3 (Abcam, ab9053), anti-H4K8acetyl (Abcam, ab1760), anti-H3K27me3 (Millipore, 07-449), anti-H3K9acetyl (Abcam, ab4441) and anti-acetyl H3 (Millipore 06-599).

Viral Integration

All the cell populations (not infected MEFs, infected MEFs and MEFs that have been infected, permeabilized and incubated with M phase *Xenopus* egg extracts or buffer) were harvested 21 days after infection and total DNA was extracted with the DNEasy kit according to the manufacturer's procedure. Quantitative PCR was then performed as described above. Quantification data were normalized to the average of two genomic regions and relative to the DNA of not infected MEFs.

```
Primers:
DNA Oct4
                                         (SEQ ID NO: 31)
Fw: aagttggcgtggagactttg (SEQ ID NO: 32)
Rev: tctgagttgctttccactcg DNA Klf4
                                         (SEQ ID NO: 33)
Fw: gctcctctacagccgagaatc (SEQ ID NO: 34)
Rev: atgtccgccaggttgaag DNA Sox2
                                         (SEQ ID NO: 35)
Fw: tcaagaggcccatgaacg (SEQ ID NO: 36)
Rev: ttgctgatctccgagttgtg DNA cMyc
                                         (SEQ ID NO: 37)
Fw: gctggagatgatgaccgagt (SEQ ID NO: 38)
Rev: atcgcagatgaagctctggt DNA genomic1
                                         (SEQ ID NO: 39)
Fw: gtcaccgtttgtgccgaa (SEQ ID NO: 40)
Rev: agctgaaatgagaccgattatgg DNA genomic2
                                         (SEQ ID NO: 41)
Fw: gagtcaaagagtggtgaaggagttagt (SEQ ID NO: 42)
Rev: agctgacgggccttctaagtc
```

REFERENCES OF EXAMPLE 2

1. Yamanaka S & Blau H M (2010) Nuclear reprogramming to a pluripotent state by three approaches. (Translated from eng) *Nature* 465(7299):704-712 (in eng).
2. Jaenisch R & Young R (2008) Stem cells, the molecular circuitry of pluripotency and nuclear reprogramming. (Translated from eng) *Cell* 132(4):567-582 (in eng).
3. Hochedlinger K & Jaenisch R (2006) Nuclear reprogramming and pluripotency. (Translated from eng) *Nature* 441(7097):1061-1067 (in eng).
4. Gurdon J B & Melton D A (2008) Nuclear reprogramming in cells. (Translated from eng) *Science* 322(5909):1811-1815 (in eng).
5. Maherali N, et al. (2007) Directly reprogrammed fibroblasts show global epigenetic remodeling and widespread tissue contribution. (Translated from eng) *Cell Stem Cell* 1(1):55-70 (in eng).
6. Feng B, Ng J H, Heng J C, & Ng H H (2009) Molecules that promote or enhance reprogramming of somatic cells to induced pluripotent stem cells. (Translated from eng) *Cell Stem Cell* 4(4):301-312 (in eng).
7. Huangfu D, et al. (2008) Induction of pluripotent stem cells by defined factors is greatly improved by small-molecule compounds. (Translated from eng) *Nat Biotechnol* 26(7):795-797 (in eng).
8. Gurdon J & Murdoch A (2008) Nuclear transfer and iPS may work best together. (Translated from eng) *Cell Stem Cell* 2(2):135-138 (in eng).
9. Alberio R, Johnson A D, Stick R, & Campbell K H (2005) Differential nuclear remodeling of mammalian somatic cells by *Xenopus laevis* oocyte and egg cytoplasm. (Translated from eng) *Exp Cell Res* 307(1):131-141 (in eng).
10. Hansis C, Barreto G, Maltry N, & Niehrs C (2004) Nuclear reprogramming of human somatic cells by *xenopus* egg extract requires BRG1. (Translated from eng) *Curr Biol* 14(16):1475-1480 (in eng).
11. Byrne J A, Simonsson S, Western P S, & Gurdon J B (2003) Nuclei of adult mammalian somatic cells are directly reprogrammed to oct-4 stem cell gene expression by amphibian oocytes. (Translated from eng) *Curr Biol* 13(14):1206-1213 (in eng).
12. Lemaitre J M, Danis E, Pasero P, Vassetzky Y, & Mechali M (2005) Mitotic remodeling of the replicon and chromosome structure. *Cell* 123:1-15.
13. Yang X, et al. (2007) Nuclear reprogramming of cloned embryos and its implications for therapeutic cloning. (Translated from eng) *Nat Genet.* 39(3):295-302 (in eng).
14. Li X, Li Z, Jouneau A, Zhou Q, & Renard J P (2003) Nuclear transfer: progress and quandaries. (Translated from eng) *Reprod Biol Endocrinol* 1:84 (in eng).
15. Takahashi K & Yamanaka S (2006) Induction of pluripotent stem cells from mouse embryonic and adult fibroblast cultures by defined factors. *Cell* 126(4):663-676.
16. Yu J, et al. (2007) Induced pluripotent stem cell lines derived from human somatic cells. (Translated from eng) *Science* 318(5858):1917-1920 (in eng).
17. Hochedlinger K & Plath K (2009) Epigenetic reprogramming and induced pluripotency. (Translated from eng) *Development* 136(4):509-523 (in eng).
18. Wernig M, et al. (2007) In vitro reprogramming of fibroblasts into a pluripotent ES-cell-like state. *Nature* 448(7151):318-324.
19. Park I H, et al. (2008) Reprogramming of human somatic cells to pluripotency with defined factors. (Translated from eng) *Nature* 451(7175):141-146 (in eng).

20. Kanai-Azuma M, et al. (2002) Depletion of definitive gut endoderm in Sox17-null mutant mice. (Translated from eng) *Development* 129(10):2367-2379 (in eng).

21. Beddington R S, Rashbass P, & Wilson V (1992) Brachyury—a gene affecting mouse gastrulation and early organogenesis. (Translated from eng) *Dev Suppl:* 157-165 (in eng).

22. Niimi T, Hayashi Y, Futaki S, & Sekiguchi K (2004) SOX7 and SOX17 regulate the parietal endoderm-specific enhancer activity of mouse laminin alpha1 gene. (Translated from eng) *J Biol Chem* 279(36):38055-38061 (in eng).

23. Pevny L H, Sockanathan S, Placzek M, & Lovell-Badge R (1998) A role for SOX1 in neural determination. (Translated from eng) *Development* 125(10):1967-1978 (in eng).

24. Todaro G J & Green H (1963) Quantitative studies of the growth of mouse embryo cells in culture and their development into established lines. (Translated from eng) *J Cell Biol* 17:299-313 (in eng).

25. Hanna J, et al. (2009) Direct cell reprogramming is a stochastic process amenable to acceleration. (Translated from eng) *Nature* 462(7273):595-601 (in eng).

26. Bru T, et al. (2008) Rapid induction of pluripotency genes after exposure of human somatic cells to mouse ES cell extracts. (Translated from eng) *Exp Cell Res* 314(14): 2634-2642 (in eng).

27. Panorchan P, Schafer B W, Wirtz D, & Tseng Y (2004) Nuclear envelope breakdown requires overcoming the mechanical integrity of the nuclear lamina. (Translated from eng) *J Biol Chem* 279(42):43462-43467 (in eng).

28. Moir R D, Puglia K V, & Willis I M (2000) Interactions between the tetratricopeptide repeat-containing transcription factor TFIIIC131 and its ligand, TFIIIB70. Evidence for a conformational change in the complex. (Translated from eng) *J Biol Chem* 275(34):26591-26598 (in eng).

29. Wang F, Kou Z, Zhang Y, & Gao S (2007) Dynamic reprogramming of histone acetylation and methylation in the first cell cycle of cloned mouse embryos. (Translated from eng) *Biol Reprod* 77(6):1007-1016 (in eng).

30. Maalouf W E, Alberio R, & Campbell K H (2008) Differential acetylation of histone H4 lysine during development of in vitro fertilized, cloned and parthenogenetically activated bovine embryos. (Translated from eng) *Epigenetics* 3(4):199-209 (in eng).

31. Baxter J, et al. (2004) Histone hypomethylation is an indicator of epigenetic plasticity in quiescent lymphocytes. (Translated from eng) *Embo J* 23(22):4462-4472 (in eng).

32. Santos F, et al. (2003) Epigenetic marking correlates with developmental potential in cloned bovine preimplantation embryos. (Translated from eng) *Curr Biol* 13(13): 1116-1121 (in eng).

33. Ng R K & Gurdon J B (2008) Epigenetic memory of an active gene state depends on histone H3.3 incorporation into chromatin in the absence of transcription. (Translated from eng) *Nat Cell Biol* 10(1):102-109 (in eng).

34. Hanna J H, Saha K, & Jaenisch R (2010) Pluripotency and cellular reprogramming: facts, hypotheses, unresolved issues. (Translated from eng) *Cell* 143(4):508-525 (in eng).

35. Egli D, Rosains J, Birkhoff G, & Eggan K (2007) Developmental reprogramming after chromosome transfer into mitotic mouse zygotes. (Translated from eng) *Nature* 447(7145):679-685 (in eng).

36. Gurdon J B & Laskey R A (1970) The transplantation of nuclei from single cultured cells into enucleate frogs' eggs. (Translated from eng) *J Embryol Exp Morphol* 24(2):227-248 (in eng).

37. Wakayama T, Tateno H, Mombaerts P, & Yanagimachi R (2000) Nuclear transfer into mouse zygotes. (Translated from eng) *Nat Genet* 24(2):108-109 (in eng).

38. Egli D, Birkhoff G, & Eggan K (2008) Mediators of reprogramming: transcription factors and transitions through mitosis. (Translated from eng) *Nat Rev Mol Cell Biol* 9(7):505-516 (in eng).

39. Kikyo N, Wade P A, Guschin D, Ge H, & Wolffe A P (2000) Active Remodeling of Somatic Nuclei in Egg Cytoplasm by the Nucleosomal ATPase ISWI. *Science* 289(5488):2360-2363.

40. Bernstein B E, et al. (2006) A bivalent chromatin structure marks key developmental genes in embryonic stem cells. (Translated from eng) *Cell* 125(2):315-326 (in eng).

41. Bui H T, Van Thuan N, Wakayama T, & Miyano T (2006) Chromatin remodeling in somatic cells injected into mature pig oocytes. (Translated from eng) *Reproduction* 131(6):1037-1049 (in eng).

42. Yeom Y I, et al. (1996) Germline regulatory element of Oct-4 specific for the totipotent cycle of embryonal cells. (Translated from eng) *Development* 122(3):881-894 (in eng).

43. Menut S, Lemaitre J M, Hair A, & Méchali M (1999) DNA replication and chromatin assembly using *Xenopus* egg extracts. *Advances in Molecular Biology: A comparative Methods Approach to the Study of Ooocytes and Embryos*, ed Richter J D (Oxford University Press), pp 196-226.

44. Taranger C K, et al. (2005) Induction of dedifferentiation, genomewide transcriptional programming, and epigenetic reprogramming by extracts of carcinoma and embryonic stem cells. (Translated from eng) *Mol Biol Cell* 16(12):5719-5735 (in eng).

45. Zhou Q, Jouneau A, Brochard V, Adenot P, & Renard J P (2001) Developmental potential of mouse embryos reconstructed from metaphase embryonic stem cell nuclei. (Translated from eng) *Biol Reprod* 65(2):412-419 (in eng).

46. Irizarry R A, et al. (2003) Exploration, normalization, and summaries of high density oligonucleotide array probe level data. (Translated from eng) *Biostatistics* 4(2): 249-264 (in eng).

47. Smyth G K (2004) Linear models and empirical bayes methods for assessing differential expression in microarray experiments. (Translated from eng) *Stat Appl Genet Mol Biol* 3:Article3 (in eng).

48. Benjamini Y & Hochberg Y (1995) Controlling the false discovery rate: a practical and powerful approach to multiple testing. *JRSSB* 57:289-300.

49. Arnaud P, et al. (2006) Stochastic imprinting in the progeny of Dnmt3L-/- females. (Translated from eng) *Hum Mol Genet.* 15(4):589-598 (in eng).

The invention claimed is:

1. A method for obtaining fully reprogrammed mammalian iPS cells comprising:
   incubating at least one permeabilized nucleus of a mammalian induced pluripotent stem (iPS) cell, or at least one permeabilized, isolated mammalian iPS cell comprising said nucleus, with an isolated extract of *Xenopus* oocytes, said oocytes blocked at metaphase II of meiosis, wherein said extract comprises EGTA;
   wherein the isolated mammalian iPS cell is produced by reprogramming of a mammalian somatic cell with retroviral vectors encoding Oct-4, Sox-2, Klf-4 and c-myc;
   wherein the method produces a higher yield of fully reprogrammed iPS cells as compared to mammalian iPS cells produced by the same method but without incubation in said extract.

2. A composition comprising: at least one permeabilized nucleus of a mammalian induced pluripotent stem (iPS) cell, or at least one permeabilized, isolated mammalian iPS cell comprising said nucleus: wherein the isolated mammalian iPS cell is produced by reprogramming of a mammalian somatic cell with retroviral vectors encoding Oct-4, Sox-2, Klf-4 and c-myc;
   an isolated extract of *Xenopus* oocytes, said oocytes blocked at metaphase II of meiosis, wherein said extract comprises EGTA.

* * * * *

SEQUENCE LISTING

<160> NUMBER OF SEQ ID NOS: 42

<210> SEQ ID NO 1
<211> LENGTH: 30
<212> TYPE: DNA
<213> ORGANISM: Artificial Sequence
<220> FEATURE:
<223> OTHER INFORMATION: forward oligonucleotide derived from Oct4

<400> SEQUENCE: 1
ttctggcgcc ggttacagaa ccatactcga                                      30

<210> SEQ ID NO 2
<211> LENGTH: 30
<212> TYPE: DNA
<213> ORGANISM: Artificial Sequence
<220> FEATURE:
<223> OTHER INFORMATION: reverse oligonucleotide derived from Oct4

<400> SEQUENCE: 2
gaggaagccg acaacaatga gaaccttcag                                      30

<210> SEQ ID NO 3
<211> LENGTH: 20
<212> TYPE: DNA
<213> ORGANISM: Artificial Sequence
<220> FEATURE:
<223> OTHER INFORMATION: forward oligonucleotide derived from Rex1

<400> SEQUENCE: 3
cagctcctgc acacagaaga                                                 20

<210> SEQ ID NO 4
<211> LENGTH: 19
<212> TYPE: DNA
<213> ORGANISM: Artificial Sequence
<220> FEATURE:
<223> OTHER INFORMATION: reverse oligonucleotide derived from Rex1

<400> SEQUENCE: 4
actgatccgc aaacacctg                                                  19

<210> SEQ ID NO 5
<211> LENGTH: 21
<212> TYPE: DNA
<213> ORGANISM: Artificial Sequence
<220> FEATURE:
<223> OTHER INFORMATION: forward oligonucleotide derived from Nanog

<400> SEQUENCE: 5
ttcttgctta caagggtctg c                                               21

<210> SEQ ID NO 6
<211> LENGTH: 18
<212> TYPE: DNA
<213> ORGANISM: Artificial Sequence
<220> FEATURE:
<223> OTHER INFORMATION: reverse oligonucleotide derived from Nanog

<400> SEQUENCE: 6
agaggaaggg cgaggaga                                                   18

<210> SEQ ID NO 7
<211> LENGTH: 20
<212> TYPE: DNA
<213> ORGANISM: Artificial Sequence

```
<220> FEATURE:
<223> OTHER INFORMATION: forward oligonucleotide derived from Zfpm2

<400> SEQUENCE: 7
gcgaagacgt ggagttcttt                                                  20

<210> SEQ ID NO 8
<211> LENGTH: 19
<212> TYPE: DNA
<213> ORGANISM: Artificial Sequence
<220> FEATURE:
<223> OTHER INFORMATION: reverse oligonucleotide derived from Zfpm2

<400> SEQUENCE: 8
ggctgtcccc atctgattc                                                   19

<210> SEQ ID NO 9
<211> LENGTH: 22
<212> TYPE: DNA
<213> ORGANISM: Artificial Sequence
<220> FEATURE:
<223> OTHER INFORMATION: forward oligonucleotide derived from beta-actin

<400> SEQUENCE: 9
gccggcttac actgcgcttc tt                                               22

<210> SEQ ID NO 10
<211> LENGTH: 20
<212> TYPE: DNA
<213> ORGANISM: Artificial Sequence
<220> FEATURE:
<223> OTHER INFORMATION: reverse oligonucleotide derived from beta-actin

<400> SEQUENCE: 10
ttctggccca tgcccaccat                                                  20

<210> SEQ ID NO 11
<211> LENGTH: 21
<212> TYPE: DNA
<213> ORGANISM: Artificial Sequence
<220> FEATURE:
<223> OTHER INFORMATION: forward oligonucleotide derived from GAPDH

<400> SEQUENCE: 11
tggcaaagtg gagattgttg c                                                21

<210> SEQ ID NO 12
<211> LENGTH: 21
<212> TYPE: DNA
<213> ORGANISM: Artificial Sequence
<220> FEATURE:
<223> OTHER INFORMATION: reverse oligonucleotide derived from GAPDH

<400> SEQUENCE: 12
aagatggtga tgggcttccc g                                                21

<210> SEQ ID NO 13
<211> LENGTH: 18
<212> TYPE: DNA
<213> ORGANISM: Artificial Sequence
<220> FEATURE:
<223> OTHER INFORMATION: forward oligonucleotide derived from Hprt1

<400> SEQUENCE: 13
tcctcctcag accgcttt                                                    18
```

```
<210> SEQ ID NO 14
<211> LENGTH: 18
<212> TYPE: DNA
<213> ORGANISM: Artificial Sequence
<220> FEATURE:
<223> OTHER INFORMATION: reverse oligonucleotide derived from Hprt1

<400> SEQUENCE: 14
cctggttcat cgctaatc                                                 18

<210> SEQ ID NO 15
<211> LENGTH: 18
<212> TYPE: DNA
<213> ORGANISM: Artificial Sequence
<220> FEATURE:
<223> OTHER INFORMATION: forward oligonucleotide derived from Sox1

<400> SEQUENCE: 15
gtgacatctg cccccatc                                                 18

<210> SEQ ID NO 16
<211> LENGTH: 19
<212> TYPE: DNA
<213> ORGANISM: Artificial Sequence
<220> FEATURE:
<223> OTHER INFORMATION: reverse oligonucleotide derived from Sox1

<400> SEQUENCE: 16
gaggccagtc tggtgtcag                                                19

<210> SEQ ID NO 17
<211> LENGTH: 20
<212> TYPE: DNA
<213> ORGANISM: Artificial Sequence
<220> FEATURE:
<223> OTHER INFORMATION: forward oligonucleotide derived from Sox 17

<400> SEQUENCE: 17
ctttatggtg tgggccaaag                                               20

<210> SEQ ID NO 18
<211> LENGTH: 20
<212> TYPE: DNA
<213> ORGANISM: Artificial Sequence
<220> FEATURE:
<223> OTHER INFORMATION: reverse oligonucleotide derived from Sox 17

<400> SEQUENCE: 18
ggtcaacgcc ttccaagact                                               20

<210> SEQ ID NO 19
<211> LENGTH: 18
<212> TYPE: DNA
<213> ORGANISM: Artificial Sequence
<220> FEATURE:
<223> OTHER INFORMATION: forward oligonucleotide derived from Sox7

<400> SEQUENCE: 19
gcggagctca gcaagatg                                                 18

<210> SEQ ID NO 20
<211> LENGTH: 20
<212> TYPE: DNA
<213> ORGANISM: Artificial Sequence
<220> FEATURE:
<223> OTHER INFORMATION: reverse oligonucleotide derived from Sox7
```

```
<400> SEQUENCE: 20
gggtctcttc tgggacagtg                                              20

<210> SEQ ID NO 21
<211> LENGTH: 20
<212> TYPE: DNA
<213> ORGANISM: Artificial Sequence
<220> FEATURE:
<223> OTHER INFORMATION: forward oligonucleotide derived from Brachyury

<400> SEQUENCE: 21
cagcccacct actggctcta                                              20

<210> SEQ ID NO 22
<211> LENGTH: 18
<212> TYPE: DNA
<213> ORGANISM: Artificial Sequence
<220> FEATURE:
<223> OTHER INFORMATION: reverse oligonucleotide derived from Brachyury

<400> SEQUENCE: 22
gagcctgggg tgatggta                                                18

<210> SEQ ID NO 23
<211> LENGTH: 18
<212> TYPE: DNA
<213> ORGANISM: Artificial Sequence
<220> FEATURE:
<223> OTHER INFORMATION: forward oligonucleotide derived from Klf4

<400> SEQUENCE: 23
gagttcctca cgccaacg                                                18

<210> SEQ ID NO 24
<211> LENGTH: 19
<212> TYPE: DNA
<213> ORGANISM: Artificial Sequence
<220> FEATURE:
<223> OTHER INFORMATION: reverse oligonucleotide derived from Klf4

<400> SEQUENCE: 24
cgggaaggga gaagacact                                               19

<210> SEQ ID NO 25
<211> LENGTH: 31
<212> TYPE: DNA
<213> ORGANISM: Artificial Sequence
<220> FEATURE:
<223> OTHER INFORMATION: forward oligonucleotide derived from Oct4 for
      bisulfite sequencing

<400> SEQUENCE: 25
ttagaggatg gttgagtggg tttgtaagga t                                 31

<210> SEQ ID NO 26
<211> LENGTH: 30
<212> TYPE: DNA
<213> ORGANISM: Artificial Sequence
<220> FEATURE:
<223> OTHER INFORMATION: reverse oligonucleotide derived from Oct4 for
      bisulfite sequencing

<400> SEQUENCE: 26
ccaatcccac cctctaacct taacctctaa                                   30
```

```
<210> SEQ ID NO 27
<211> LENGTH: 30
<212> TYPE: DNA
<213> ORGANISM: Artificial Sequence
<220> FEATURE:
<223> OTHER INFORMATION: forward oligonucleotide derived from Nanog for
      bisulfite sequencing

<400> SEQUENCE: 27
taaattgggt atggtggtag ataagtttgg                                          30

<210> SEQ ID NO 28
<211> LENGTH: 30
<212> TYPE: DNA
<213> ORGANISM: Artificial Sequence
<220> FEATURE:
<223> OTHER INFORMATION: reverse oligonucleotide derived from Nanog for
      bisulfite sequencing

<400> SEQUENCE: 28
taaaaaacat cctctaatct aaaaacatcc                                          30

<210> SEQ ID NO 29
<211> LENGTH: 22
<212> TYPE: DNA
<213> ORGANISM: Artificial Sequence
<220> FEATURE:
<223> OTHER INFORMATION: forward oligonucleotide derived from Snrnp for
      bisulfite sequencing

<400> SEQUENCE: 29
attggtgagt taatttttg ga                                                   22

<210> SEQ ID NO 30
<211> LENGTH: 22
<212> TYPE: DNA
<213> ORGANISM: Artificial Sequence
<220> FEATURE:
<223> OTHER INFORMATION: reverse oligonucleotide derived from Snrnp for
      bisulfite sequencing

<400> SEQUENCE: 30
acaaaactcc tacatcctaa aa                                                  22

<210> SEQ ID NO 31
<211> LENGTH: 20
<212> TYPE: DNA
<213> ORGANISM: Artificial Sequence
<220> FEATURE:
<223> OTHER INFORMATION: forward oligonucleotide derived from Oct4 for
      quantifying integration

<400> SEQUENCE: 31
aagttggcgt ggagactttg                                                     20

<210> SEQ ID NO 32
<211> LENGTH: 20
<212> TYPE: DNA
<213> ORGANISM: Artificial Sequence
<220> FEATURE:
<223> OTHER INFORMATION: reverse oligonucleotide derived from Oct4 for
      quantifying integration

<400> SEQUENCE: 32
tctgagttgc tttccactcg                                                     20
```

<210> SEQ ID NO 33
<211> LENGTH: 21
<212> TYPE: DNA
<213> ORGANISM: Artificial Sequence
<220> FEATURE:
<223> OTHER INFORMATION: forward oligonucleotide derived from Klf4 for
      quantifying integration

<400> SEQUENCE: 33
gctcctctac agccgagaat c                                              21

<210> SEQ ID NO 34
<211> LENGTH: 18
<212> TYPE: DNA
<213> ORGANISM: Artificial Sequence
<220> FEATURE:
<223> OTHER INFORMATION: reverse oligonucleotide derived from Klf4 for
      quantifying integration

<400> SEQUENCE: 34
atgtccgcca ggttgaag                                                  18

<210> SEQ ID NO 35
<211> LENGTH: 18
<212> TYPE: DNA
<213> ORGANISM: Artificial Sequence
<220> FEATURE:
<223> OTHER INFORMATION: forward oligonucleotide derived from Sox2 for
      quantifying integration

<400> SEQUENCE: 35
tcaagaggcc catgaacg                                                  18

<210> SEQ ID NO 36
<211> LENGTH: 20
<212> TYPE: DNA
<213> ORGANISM: Artificial Sequence
<220> FEATURE:
<223> OTHER INFORMATION: reverse oligonucleotide derived from Sox2 for
      quantifying integration

<400> SEQUENCE: 36
ttgctgatct ccgagttgtg                                                20

<210> SEQ ID NO 37
<211> LENGTH: 20
<212> TYPE: DNA
<213> ORGANISM: Artificial Sequence
<220> FEATURE:
<223> OTHER INFORMATION: forward oligonucleotide derived from cMyc for
      quantifying integration

<400> SEQUENCE: 37
gctggagatg atgaccgagt                                                20

<210> SEQ ID NO 38
<211> LENGTH: 20
<212> TYPE: DNA
<213> ORGANISM: Artificial Sequence
<220> FEATURE:
<223> OTHER INFORMATION: reverse oligonucleotide derived from cMyc for
      quantifying integration

<400> SEQUENCE: 38
atcgcagatg aagctctggt                                                20

<210> SEQ ID NO 39

```
<211> LENGTH: 18
<212> TYPE: DNA
<213> ORGANISM: Artificial Sequence
<220> FEATURE:
<223> OTHER INFORMATION: forward oligonucleotide derived from genomic
      region 1

<400> SEQUENCE: 39
gtcaccgttt gtgccgaa                                                        18

<210> SEQ ID NO 40
<211> LENGTH: 23
<212> TYPE: DNA
<213> ORGANISM: Artificial Sequence
<220> FEATURE:
<223> OTHER INFORMATION: reverse oligonucleotide derived from genomic
      region 1

<400> SEQUENCE: 40
agctgaaatg agaccgatta tgg                                                  23

<210> SEQ ID NO 41
<211> LENGTH: 27
<212> TYPE: DNA
<213> ORGANISM: Artificial Sequence
<220> FEATURE:
<223> OTHER INFORMATION: forward oligonucleotide derived from genomic
      region 2

<400> SEQUENCE: 41
gagtcaaaga gtggtgaagg agttagt                                              27

<210> SEQ ID NO 42
<211> LENGTH: 21
<212> TYPE: DNA
<213> ORGANISM: Artificial Sequence
<220> FEATURE:
<223> OTHER INFORMATION: reverse oligonucleotide derived from genomic
      region 2

<400> SEQUENCE: 42
agctgacggg ccttctaagt c                                                    21
```